(12) United States Patent
Frank et al.

(10) Patent No.: US 8,101,347 B2
(45) Date of Patent: Jan. 24, 2012

(54) **METHOD AND COMPOSITIONS FOR IMMUNIZATION WITH THE *PSEUDOMONAS* V ANTIGEN**

(75) Inventors: Dara W. Frank, West Allis, WI (US); Jeannine Wiener-Kronish, San Francisco, CA (US); Timothy L. Yahr, Coralville, IA (US); Teiji Sawa, San Francisco, CA (US); Robert B. Fritz, Milwaukee, WI (US)

(73) Assignee: MCW Research Foundation, Inc., Milwaukee, WI (US)

( * ) Notice: Subject to any disclaimer, the term of this patent is extended or adjusted under 35 U.S.C. 154(b) by 0 days.

(21) Appl. No.: 12/355,614

(22) Filed: Jan. 16, 2009

(65) Prior Publication Data

US 2009/0191241 A1    Jul. 30, 2009

Related U.S. Application Data

(63) Continuation of application No. 10/496,059, filed as application No. PCT/US02/02382 on Jan. 25, 2002, now Pat. No. 7,494,653.

(60) Provisional application No. 60/264,795, filed on Jan. 29, 2001.

(51) Int. Cl.
*C12Q 1/68* (2006.01)

(52) U.S. Cl. ....... 435/6; 536/23.7; 536/24.3; 536/24.32; 536/24.33

(58) Field of Classification Search .................. None
See application file for complete search history.

(56) References Cited

U.S. PATENT DOCUMENTS 5,599,665 A    2/1997  Barberi et al.
6,551,795 B1 *  4/2003  Rubenfield et al. .......... 435/69.1

FOREIGN PATENT DOCUMENTS

WO    00/33872 A3    6/2000
WO    0033872        6/2000

OTHER PUBLICATIONS

Yahr et al (J. Bacteriol. 179 (22), 7165-7168. 1997).*
Hauser et al (Infect. Immun. 66 (4), 1413-1420.1998).*

International Search Report for PCT/US02/02382, under date of mailing of Sep. 25, 2002.
Sawa et al., "Active and passive immunization with the Pseduomnas V antigen protects against type II intoxcation and lung injury" Nature Medicine, Nature America, New York, US; vol. 5, No. 4, 1999; pp. 392-398; DXP002142838.
Holder et al., "Abstracts of the General Meeting of the American Society for Microbiology, the Society, Washington, DC, US", No. 100, 2000, pp. 279-280; XP008007075; ISSN: 1060-2011.
Kataoka et al., "The Nucleotide Sequences of Rearranged and Germline Immunioglobulin VH Genes of a Mouse Myeloma MC101 and Evolution of VH Genes in Mouse"; Journal of Biological Chemistry vol. 257, No. 1, 1982; pp. 277-285; XP2213468; ISSN: 0021-9258.
Frank et al., "Generation and Characterization of a protective monoclonal antibody to *Pseudomopnas aeruginosa* PcrV" Journal of Infectious Diseases, vol. 186, No. 1; 2002, pp. 64-73; XP008007095; ISSN:0022-1899.
Roggenkamp et al., "Passive Immunity to Infection with . . . ", Infection & Immunity, American Society for Microbiology, vol. 65, No. 2, Feb. 1997, 0019-9867.
European Search Report dated Feb. 2, 2008 issued in EP application 06000111.2-2402.
G.W. Anderson, Jr., et al., "Recombinant V. Antigen Protects Mice Against Pneumonic and Bubonic Plague Caused by F1-Capsule-Positive and -Negative Strains of *Yersinia pestis*," Infect. Immun. 64(11):4580-4585, 1996.
H. Hahn, et al., "Pilin-Based Anti-*Pseudomonas* Vaccines; Latest Developments and Perspectives," Behring Inst. Mitt. 98:315-325, 1997.
T.L. Yahr, et al., "Indentification of Type III Secreted Products of the *Pseudomonas aeruginosa* Exoenzyme S Regulon," J. Bacteriol. 179(22):7165-7168, 1997.
Roy-Burman et al. "Type-III protein secretion is associated with death in lower respiratory and systemic *Pseudomonas aeruginosa* infections," J Infect Dis 2001;183:1767-74.
Shime et al. "Therapeutic administration of anti-PcrV F(ab')2 in sepsis associated with *Pseudomonas aeruginosa*," J Immunol 2001;167:5880-6.

* cited by examiner

*Primary Examiner* — Jennifer Graser
(74) *Attorney, Agent, or Firm* — Quarles & Brady LLP

(57) ABSTRACT

A method of inhibiting, moderating or diagnosing *Pseudomonas aeruginosa* infection is disclosed. In one embodiment, this method comprises inoculating a patient with an effective amount of PcrV antigen.

2 Claims, 9 Drawing Sheets m166 heavy chain

1. m166 heavy chain (IgG2b) complete mRNA sequence:

(From the transcriptional start point to the polyA-tail)

```
CCATCCTCTT CTCATAGAGC CTCCATCAGA GCATGGCTGT CTTGGGGCTG
CTCTTCTGCC TGGTGACATT CCCAAGCTGT GTCCTATCCC AGGTGCAGCT
GAAGCAGTCA GGACCTGGCC TAGTGCAGCC CTCACAGAGC CTGTCCATCA
CCTGCACAGT CTCTGGTTTC TCATTAACTA GCTATGGTGT ACACTGGGTT
CGTCAGTCTC CAGGAAAGGG TCTGGAGTGG CTGGGAGTGA TATGGAGTGG
TGGAGACACA GACTATAATG CAGCTTTCAT ATCCAGACTG AGCATCAGCA
AGGACAATTC CAAGAGCCAA CTCTTCTTTA AAATGAACAG TCTGCGAGCT
ACTGACACAG CCATATATTA CTGTGCCAGA AATAGAGGGG ATATTTACTA
TGATTTCACT TATGCCATGG ACTACTGGGG TCAAGGAACC TCAGTCACCG
TCTCCTCAGC CAAAACAACA CCCCCATCAG TCTATCCACT GGCCCCTGGG
TGTGGAGATA CAACTGGTTC CTCCGTGACT CTGGGATGCC TGGTCAAGGG
CTACTTCCCT GAGTCAGTGA CTGTGACTTG GAACTCTGGA TCCTGTCCA
GCAGTGTGCA CACCTTCCCA GCTCTCCTGC AGTCTGGACT CTACACTATG
AGCAGCTCAG TGACTGTCCC CTCCAGCACC TGGCCAAGTC AGACCGTCAC
CTGCAGCGTT GCTCACCCAG CCAGCAGCAC CACGGTGGAC AAAAAACTTG
AGCCCAGCGG GCCCATTTCA ACAATCAACC CCTGTCCTCC ATGCAAGGAG
TGTCACAAAT GCCCAGCTCC TAACCTCGAG GGTGGACCAT CCGTCTTCAT
CTTCCCTCCA AATATCAAGG ATGTACTCAT GATCTCCCTG ACACCCAAGG
TCACGTGTGT GGTGGTGGAT GTGAGCGAGG ATGACCCAGA CGTCCAGATC
AGCTGGTTTG TGAACAACGT GGAAGTACAC ACAGCTCAGA CACAAACCCA
TAGAGAGGAT TACAACAGTA CTATCCGGGT GGTCAGCACC CTCCCCATCC
AGCACCAGGA CTGGATGAGT GGCAAGGAGT TCAAATGCAA GGTCAACAAC
AAAGACCTCC CATCACCCAT CGAGAGAACC ATCTCAAAAA TTAAAGGGCT
AGTCAGAGCT CCACAAGTAT ACATCTTGCC GCCACCAGCA GAGCAGTTGT
CCAGGAAAGA TGTCAGTCTC ACTTGCCTGG TCGTGGGCTT CAACCCTGGA
GACATCAGTG TGGAGTGGAC CAGCAATGGG CATACAGAGG AGAACTACAA
GGACACCGCA CCAGTCCTGG ACTCTGACGG TTCTTACTTC ATATATAGCA
AGCTCAATAT GAAAACAAGC AAGTGGGAGA AAACAGATTC CTTCTCATGC
AACGTGAGAC ACGAGGGTCT GAAAATTAC TACCTGAAGA AGACCATCTC
CCGGTCTCCG GGTAAATGAG CTCAGCACCC ACAAAGCTCT CAGGTCCTAA
GAGACACTGG CACCCATATC CATGCATCCC TTGTATAAAT AAAGCATCCA
GCAAAGCCTG GTACCATGTA AAAAAAAAAA AAAAAAA
```

FIG. 6A

2. m166 heavy chain (IgG2b) complete amino acid sequence:

(From the start codon to the stop codon)

```
MAVLGLLFCL VTFPSCVLSQ VQLKQSGPGL VQPSQSLSIT CTVSGFSLTS
YGVHWVRQSP GKGLEWLGVI WSGGDTDYNA AFISRLSISK DNSKSQLFFK
MNSLRAIDTA IYYCARNRGD IYYDFTYAMD YWGQGTSVTV SSAKTTPPSV
YPLAPGCGDT TGSSVTLGCL VKGYFPESVT VTWNSGSLSS SVHTFPALLQ
SGLYTMSSSV TVPSSTWPSQ TVTCSVAHPA SSTTVDKKLE PSGPISTINP
CPPCKECHKC PAPNLEGGPS VFIFPPNIKD VLMISLTPKV TCVVVDVSED
DPDVQISWFV NNVEVHTAQT QTHREDYNST IRVVSTLPIQ HQDWMSGKEF
KCKVNNKDLP SPIERTISKI KGLVRAPQVY ILPPAEQLS RKDVSLTCLV
VGFNPGDISV EWTSNGHTEE NYKDTAPVLD SDGSYFIYSK LNMKTSKWEK
TDSFSCNVRH EGLKNYYLKK TISRSPGK[STOP]
```

[Sig-pep] MAVLGLLFCLVTFPSCVLS

[VH-region]
FR1: QVQLKQSGPGLVQPSQSLSITCTVSGFSLT
CDR1: SYGVH
FR2: WVRQSPGKGLEWLG
CDR2: VIWSGGDTDYNAAFIS
FR3: RLSISKDNSKSQLFFKMNSLRAIDTAIYYCAR
CDR3: NRGDIYYDFTYAMDY
FR4: WGQGTSVTVSS

[CH-region]
CH:
```
AKTTPPSVYP LAPGCGDTTG SSVTLGCLVK GYFPESVTVT WNSGSLSSSV
HTFPALLQSG LYTMSSSVTV PSSTWPSQTV TCSVAHPASS TTVDKKLEPS
GPISTINPCP PCKECHKCPA PNLEGGPSVF IFPPNIKDVL MISLTPKVTC
VVVDVSEDDP DVQISWFVNN VEVHTAQTQT HREDYNSTIR VVSTLPIQHQ
DWMSGKEFKC KVNNKDLPSP IERTISKIKG LVRAPQVYIL PPPAEQLSRK
DVSLTCLVVG FNPGDISVEW TSNGHTEENY KDTAPVLDSD GSYFIYSKLN
MKTSKWEKTD SFSCNVRHEG LKNYYLKKTI SRSPGK[STOP]
```

FIG. 6B m166 light chain

1. m166 light chain (k) complete mRNA sequence:

(From the transcriptional start point to the polyA tail)

```
ACACCCTTTG CTGGAGTCAG AATCACACTG ATCACACACA GTCATGAGTG
TGCTCACTCA GGTCCTGGCG TTGCTGCTGC TGTGGCTTAC AGGTGCCAGA
TGTGACATCC AGATGACTCA GTCTCCAGCC TCCCTATCTG CATCTGTGGG
AGAAACTGTC ACCATCACAT GTCGAGCAAG TGGGAATATT CAAATTATT
TAGCATGGTA TCAGCAGACA CAGGGAAAAT CTCCTCAGCT CCTGGTCTAT
TCTGCAAAAA CCTTAGCAGA TGGTGTGCCA TCAAGGTTCA GTGGCAGTGG
ATCAGGAACA CAATATTCTC TCAAGATCAA CAGCCTGCAG CCTGAAGATT
TTGGAGTTA TTACTGTCAA CATTTTTGGA GTACTCCGTA CACGTTCGGA
GGGGGGACCA AGCTGGAAAT AAAACGGGCT GATGCTGCAC CAACTGTATC
CATCTTCCCA CCATCCAGTG AGCAGTTAAC ATCTGGAGGT GCCTCAGTCG
TGTGCTTCTT GAACAACTTC TACCCCAAAG ACATCAATGT CAAGTGGAAG
ATTGATGGCA GTGAACGACA AAATGGCGTC CTGAACAGTT GGACTGATCA
GGACAGCAAA GACAGCACCT ACAGCATGAG CAGCACCCTC ACGTTGACCA
AGGACGAGTA TGAACGACAT AACAGCTATA CCTGTGAGGC CACTCACAAG
ACATCAACTT CACCCATTGT CAAGAGCTTC AACAGGAATG AGTGTTAGAG
ACAAAGGTCC TGAGACGCCA CCACCAGCTC CCCAGCTCCA TCCTATCTTC
CCTTCTAAGG TCTTGGAGGC TTCCCCACAA GCGACCTACC ACTGTTGCGG
TGCTCCAAAC CTCCTCCCCA CCTCCTTCTC CTCCTCCTCC CTTTCCTTGG
CTTTATCAT GCTAATATTT GCAGAAAATA TTCAATAAAG TGAGTCTTTG
CAAAAAAAAA AAAAAAAAAA AAAAAAAA
```

2. m166 light chain (k) amino acid complete sequence:

(From the start codon to the stop codon)

```
MSVLTQVLAL LLLWLTGARC DIQMTQSPAS LSASVGETVT ITCRASGNIQ
NYLAWYQQTQ GKSPQLLVYS AKTLADGVPS RFSGSGSGTQ YSLKINSLQP
EDFGSYYCQH FWSTPYTFGG GTKLEIKRAD AAPTVSIFPP SSEQLTSGGA
SVVCFLNNFY PKDINVKWKI DGSERQNGVL NSWTDQDSKD STYSMSSTLT
LTKDEYERHN SYTCEATHKT STSPIVKSFN RNEC[STOP]
```

[Sig-pep] MSVLTQVLALLLLWLTGARC

[VL-region]
FR1: DIQMTQSPASLSASVGETVTITC
CDR1: RASGNIQNYLA
FR2: WYQQTQGKSPQLLVY
CDR2: SAKTLAD
FR3: GVPSRFSGSGSGTQYSLKINSLQPEDFGSYYC
CDR3: QHFWSTPYT
FR4: FGGGTKLEIKR

[CL-region]
CL: ADAAPTVSIFPPSSEQLTSGGASVVCFLNNFYPKDINVKWKIDGSERQNGVL
NSWTDQDSKDSTYSMSSTLTLTKDEYERHNSYTCEATHKTSTSPIVKSFNRNEC[STOP]

FIG. 7

Synthetic recombinant single chain antibody (scFv-m166)

1. DNA sequence:

```
ATGAAAAAAC TGCTGTTCGC GATTCCGCTG GTGGTGCCGT TCTATAGCCA
TAGCACCATG GAGCTCGAGC GGCAGGTGCA GCTGAAGCAG TCAGGACCTG
GCCTAGTGCG GCCCTCACAG AGCCTGTCCA TCACCTGCAC AGTCTCTGGT
TTCTCATTAA CTAGCTATGG TGTACACTGG GTTCGTCAGT CTCCAGGAAA
GGGTCTGGAG TGGCTGGGAG TGATATGGAG TGGTGGAGAC ACAGACTATA
ATGCAGCTTT CATATCCAGA CTGAGCATCA GCAAGGACAA TTCCAAGAGC
CAACTCTTCT TTAAAATGAA CAGTCTGCGA GCTACTGACA CAGCCATATA
TTACTGTGCC AGAAATAGAG GGGATATTTA CTATGATTTC ACTTATGCCA
TGGACTACTG GGGTCAAGGA ACCTCAGTCA CCGTCTCCTC AGGTGGAGGC
GGCTCAGGCG GAGGTGGCTC TGGCGGTGGC GGATCGGACA TCCAGATGAC
TCAGTCTCCA GCCTCCCTAT CTGCATCTGT GGGAGAAACT GTCACCATCA
CATGTCGAGC AAGTGGGAAT ATTCAAAATT ATTTAGCATG GTATCAGCAG
ACACAGGGAA AATCTCCTCA GCTCCTGGTC TATTCTGCAA AAACCTTAGC
AGATGGTGTG CCATCAAGGT TCAGTGGCAG TGGATCAGGA ACACAATATT
CTCTCAAGAT CAACAGCCTG CAGCCTGAAG ATTTTGGGAG TTATTACTGT
CAACATTTTT GGAGTACTCC GTACACGTTC GGAGGGGGGA CCAAGCTGGA
AATAAAACGG GCTCTAGAAC AAAAACTCAT CTCAGAAGAG GATCTGAATA
GCGCCGTCGA CCATCATCAT CATCATCATT GA
```

2. Amino acid sequence:

```
MKKLLFAIPL VVPFYSHSTM ELERQVQLKQ SGPGLVRPSQ SLSITCTVSG
FSLTSYGVHW VRQSPGKGLE WLGVIWSGGD TDYNAAFISR LSISKDNSKS
QLFFKMNSLR ATDTAIYYCA RNRGDIYYDF TYAMDYWGQG TSVTVSSGGG
GSGGGGSGGG GSDIQMTQSP ASLSASVGET VTITCRASGN IQNYLAWYQQ
TQGKSPQLLV YSAKTLADGV PSRFSGSGSG TQYSLKINSL QPEDFGSYYC
QHFWSTPYTF GGGTKLEIKR ALEQKLISEE DLNSAVDHHH HHH[STOP]
```

[Gene III signal sequence] MKKLLFAIPLVVPFYSHS
[Joint-1] TMELER
[m166 heavy chain]
QVQLKQSGPG LVRPSQSLSI TCTVSGFSLT SYGVHWVRQS PGKGLEWLGV
IWSGGDTDYN AAFISRLSIS KDNSKSQLFF KMNSLRATDT AIYYCARNRG
DIYYDFTYAM DYWGQGTSVT VSS
[scFv-linker] GGGGSGGGGSGGGGS
[m166 light chain]
DIQMTQSPAS LSASVGETVT ITCRASGNIQ NYLAWYQQTQ GKSPQLLVYS
AKTLADGVPS RFSGSGSGTQ YSLKINSLQP EDFGSYYCQH FWSTPYTFGG
GTKLEIKR
[Joint-2] AL
[Myc epitope] EQKLISEEDL
[Joint-3] NSAVD
[Hexahistidine tag] HHHHHH [STOP]

FIG. 8

METHOD AND COMPOSITIONS FOR IMMUNIZATION WITH THE *PSEUDOMONAS* V ANTIGEN

CROSS-REFERENCE TO RELATED APPLICATION

The present application is a continuation of U.S. patent application Ser. No. 10/496,059, filed Nov. 11, 2004 and issued as U.S. Pat. No. 7,494,653 on Feb. 24, 2009, which is a 371 of PCT/US02/02382, filed Jan. 25, 2002 and claims priority of U.S. patent application Ser. No. 09/770,916, filed Jan. 26, 2001 and issued as U.S. Pat. No. 6,827,935 on Dec. 7, 2004, and U.S. provisional patent application 60/264,795, filed Jan. 29, 2001. These documents are incorporated by reference herein.

STATEMENT REGARDING FEDERALLY SPONSORED RESEARCH OR DEVELOPMENT

This invention was made with United States government support awarded by the following agencies: NIH/NIADA Grant Nos. R01 A131665-08, K04 A101289-04 and R01 HL59239-02. The United States has certain rights in this invention.

BACKGROUND OF THE INVENTION

*Pseudomonas aeruginosa* is an opportunistic bacterial pathogen that is capable of causing fatal acute lung infections in critically ill individuals (1). The ability of the bacterium to damage the lung epithelium has been linked with the expression of toxins that are directly injected into eukaryotic cells via a type III-mediated secretion and translocation mechanism (2,3).

The proteins encoded by the *P. aeruginosa* type III secretion and translocation apparatus demonstrate a high level of amino acid identity with members of the *Yersinia* Yop regulon (4-6). Of all the type III systems discovered in Gram-negative bacteria, only *P. aeruginosa* possesses a homologue to the *Yersinia* V antigen, PcrV (see 6 for review of type III systems). Homologous proteins to the secretion and translocation apparatus are encoded by both plant and animal pathogenic bacteria. These organisms include human pathogens such as *Salmonella typhimurium, Shigella flexneri*, Enteropathogenic *E. coli, Chlamydia* spp., and plant pathogens such as *Xanthamonas campestris, Pseudomonas* syringe, *Erwinia amylovora* and *Ralstonia solanacearum*. However, only *P. aeruginosa* and *Yersinia* encode the V antigen.

Yahr, et al., 1997, discloses the sequence of the operon encoding PcrV and compares the sequence to the LcrV protein. Thus, the nucleic acid sequence of PcrV is known and is available under accession number AF010149 of GenBank (SEQ ID NO:8).

DESCRIPTION OF THE DRAWINGS

FIGS. 6A and B are printouts of SEQ ID NOs:1 and 2 with additional explanatory information. FIG. 6A is SEQ ID NO:1. FIG. 6B is SEQ ID NO:2.

FIG. 7 is a printout of SEQ ID NOs:3 and 4 with additional explanatory information.

FIG. 8 is a synthetic recombinant single chain antibody (SCFV-M166) (SEQ ID NOs:5 and 6).

SUMMARY OF THE INVENTION

Figure 1:
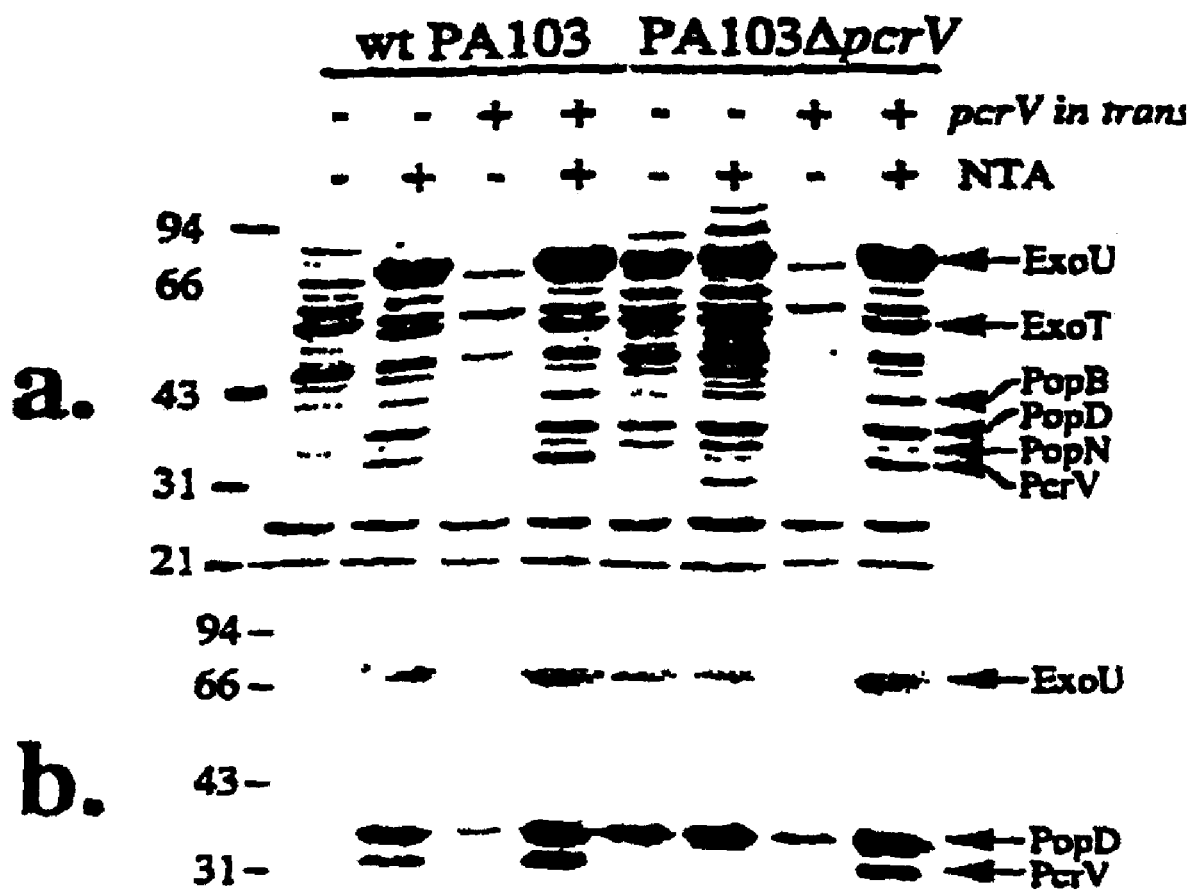
FIGS. 1A and 1B are a stained gel (FIG. 1A) and Western blot (FIG. 1B) illustrating the phenotypic analysis of PA103ApcrV.

The present invention involves methods and compositions developed from our observation that the *Pseudomonas* V antigen can be used to protect animals from a lethal lung infection.

In one embodiment, the present invention is a method of inhibiting *Pseudomonas* infection comprising inoculating a patient with an effective amount of PcrV antigen. In another embodiment, DNA encoding PcrV is used as a gene vaccine.

In one preferred embodiment, the antigen is expressed as a recombinant protein and used to immunize patients at risk.

Preferably, the patient is completely protected from infection.

In another embodiment, the DNA encoding PcrV (called pcrv) or a DNA fragment may be used diagnostically to detect *P. aeruginosa* infection.

In another embodiment, the recombinant protein (rPcrV) is used diagnostically to detect antibodies from patients. Patient antibody response to PcrV may be associated with prognosis. Therefore, in this embodiment the recombinant protein is used as a prognostic indicator by measuring the patient's antibody titer.

The present invention also provides a method for inhibiting a *Pseudomonas* infection in an individual by contacting the individual with an effective amount of a PcrV inhibitor, in particular with a PcrV antibody, antibody derivative or fragment, or antibody mimic. PcrV antibodies, antibody derivatives and antibody fragments are also provided.

It is an object of the present invention to actively and passively immunize a patient against *Pseudomonas* infection.

It is another object of the present invention to diagnostically detect the *P. aeruginosa* infection.

It is another object of the present invention to diagnostically detect antibodies from *Pseudomonas* patients.

Other objects, features and advantages of the present invention will become apparent to one of skill in the art after review of the specification, claims and drawings.

DESCRIPTION OF THE INVENTION

We disclose herein that PcrV has a novel regulatory effect on expression of the type III secreted products, is involved in the translocation of type III toxins, and is the first antigen that protects against lung injury induced by *P. aeruginosa* infection. Vaccination against PcrV prior to the airspace instillation of anti-PcrV IgG not only ensured the survival of challenged animals but also decreased lung inflammation and injury caused by the bacteria.

LcrV, or the V antigen, is a multifunctional protein that regulates secretion/translocation of the Yop effector proteins and plays an extracellular role in pathogenesis by altering the host cytokine response to *Yersinia* infection (7-11). The only known homologue of this critical pathogenic factor is an extracellular protein encoded by *P. aeruginosa*, termed PcrV.

One embodiment of the present invention is a method of moderating or inhibiting a *Pseudomonas* infection by immunizing a patient with an effective amount of the PcrV antigen. By "effective amount" we mean an amount of PcrV antigen effective to show some moderation or inhibition of *Pseudomonas* infection as compared to control subjects or animals who have not been treated with the antigen.

By "moderating" we mean that infection is inhibited by at least fifty percent compared to a non-immunized animal. Preferably, infection is completely prevented. A quantitative assessment of infection would preferably include the examination of the amount of bacteria in the bloodstream or pleural fluids and/or an examination of lung injury parameters. For example, the absence of bacteria in the bloodstream or pleural fluids would indicate prevention of infection. A reduction in lung injury parameters would indicate that infection is moderated.

Infection could be quantitatively assessed by several other clinical indicators, including the reduction of bacterial load in the sputum, blood or pleural fluids, reduction in the size of the infiltrate, oxygenation improvement, reduction in the length of time on mechanical ventilation, reduction in fever and reduction in white blood cell count.

By "PcrV antigen" we mean that portion or fragment of the PcrV protein that is necessary to invoke an immune response which prevents or moderates infection. We have used the full-length PcrV protein as an antigen to induce protection. Additionally, we have mapped the protective epitope to the fragment comprising amino acids 144-257 of PcrV (SEQ ID NO:7). To define the epitope, monoclonal antibodies that protected against infection and cytotoxicity were tested for binding to progressively smaller forms of recombinant PcrV. (By "recombinant PcrV" or "rPcrV" we mean the protein produced from a PcrV gene that has been placed in a non-native host.) This protection localized the region.

The PcrV antigen may be most easily obtained by the method we used, commercially available bacterial expression plasmid pet16b from Novagen. The pcrV gene was first cloned from the *P. aeruginosa* chromosome as part of an operon. The coding region was amplified and inserted into two different vectors. One vector is for expression from *P. aeruginosa* as shown in FIG. 1. This is a vector from Herbert Schweizer (reference 19) which we modified to contain an appropriate promoter sequence such that PcrV expression is coordinately regulated with the rest of the delivery and intoxication apparatus of the bacterium. The second plasmid, pET16b, is for expression and purification purposes from *E. coli*.

The advantage of this system is that we do not have to worry about contaminating *P. aeruginosa* proteins, the protein is produced in great abundance, and there is a one-step purification process. In this situation the PcrV coding region is amplified to be cloned in frame with a histidine tag provided on the pET16b vector. The multiple histidine residues fused to the amino terminus of PcrV allow affinity chromatography using a nickel-NTA column. Therefore, a preferable PcrV antigen is a recombinant version of the natural PcrV protein.

Immunization may be done systemically or intranasally. Immunization of these individuals would preferably start during normal vaccination procedures for other childhood diseases. We would predict long-lived protection with booster doses probably around ages 5 and 10.

In another embodiment, one would use DNA encoding the PcrV protein or the complement of this DNA to diagnostically detect *P. aeruginosa* infection. One would obtain the DNA sequence of the PcrV antigen at GenBank AF010149. The coding region for PcrV is at nucleotides 626-1510. One may also choose to use a fragment of this coding region or complement of this fragment. A successful probe is one that will hybridize specifically to the PcrV DNA and not to other regions.

One would preferably use a hybridization probe of at least 40 continuous nucleotides within the antigen sequence or two primers of at least 25 continuous nucleotides within the sequence. One skilled in the art would appreciate that many standard forms of nucleic acid diagnostic techniques would be suitable, for example, hybridization of the single-stranded 40 nucleotide probe to DNA or RNA extracted from a patient's sputum. In another example, patient's sputum would be used as a source for bacterial DNA or RNA to serve as a template for the PCR or RT-PCR reaction, respectively.

One would also determine *Pseudomonas aeruginosa* infection in an individual by contacting a sample obtained from the individual with an antibody specific for PcrV and correlating enhanced antibody binding as compared with a control sample with *Pseudomonas aeruginosa* infection in the individual.

In an additional embodiment, the DNA encoding PcrV is used as a gene vaccine using standard molecular biological methods. For example, one could review the following references for techniques known to those of skill in the art: Davis, H. L., et al., "DNA vaccine for hepatitis B: Evidence for immunogenicity in chimpanzees and comparison with other vaccines," *Proc. Natl. Acad. Sci.* 93:7213-7218, 1996; Barry, M. A., et al., "Protection against mycoplasma infection using expression-library immunization," *Nature* 377:632-635, 1995; Xiang, Z. Q., et al., "Immune responses to nucleic acid vaccines to rabies virus," *Virology* 209:569-579, 1995. By "effective amount" of a gene vaccine, we mean an amount of vaccine effective to moderate or eliminate *Pseudomonas* infection or *Pseudomonas* infection symptoms.

The protein or antigen could also be used diagnostically to detect antibodies in patients and, thus, predict the patient's infection status. One would preferably contact a sample obtained from an individual suspected of *Pseudomonas* infection with the PcrV protein or fragment thereof and detect protein/antibody binding. One would then correlate enhanced antibody binding (as compared with a control sample) with *Pseudomonas aeruginosa* infection in the individual. One could also use the PcrV antibody or antibody fragments therapeutically.

In another embodiment, the invention is the use of the antibody sequence (which we report below and in SEQ ID NOs:1-4) to produce recombinant single chain antibodies that may block PcrV and could also utilize the sequence in gene delivery experiments, where one would deliver eukaryotic vectors that will then lead to the production of single chain antibodies in animals for prolonged periods. The sequence could also be utilized to humanize the murine monoclonal antibody to produce a product that can be utilized in human patient care.

Once the antibody is safe for human use, one could: (a) administer it systemically and (b) administer it into the lungs as either a preventative treatment or as a therapy. In order to use the PcrV antibody in humans, the antibody is preferably "humanized". In general, once the monoclonal antibody is obtained the heavy and light chain variable regions are cloned. These cloned fragments are then inserted into a human antibody backbone (constant regions). Thus, we can control the class of antibody (IgG, IgA, etc.) in addition to providing the binding specificity.

For use in the present invention, the PcrV antibody may be a monoclonal antibody or polyclonal. The antibodies may be human or humanized, particularly for therapeutic applications. Antibody fragments or derivatives, such as an Fab, F(ab')$_2$ or Fv, may also be used. Single-chain antibodies, for example as described in Huston, et al. (*Int. Rev. Immunol.* 10:195-217, 1993) may also find use in the methods described herein. By "effective amount" of the PcrV antibody or antibody fragment we mean an amount sufficient to moderate or eliminate *Pseudomonas* infection or infection symptoms.

Preferably, human or humanized monoclonal or polyclonal antibodies to PcrV are administered to prevent or treat infections with *P. aeruginosa*. In patients at high risk for *P. aeruginosa* infection, antibodies could be administered for prevention of infection. In addition, antibodies may be administered after the onset of infection to treat the infection. In this case, antibodies can be administered alone or in combination with antibiotics. Administration of antibodies in conjunction with antibiotics may allow the administration of shorter courses or lower doses of antibiotics, thereby decreasing the risk of emergence of antibiotic-resistant organisms.

We envision at least three types of hypothetical patients: (1) A healthy individual at risk of serious injury or burn (fire fighter, military personnel, police) would be immunized with the vaccine by a methodology (either injection or intranasal) that would give long-lived protection. A booster would be given on admission (intramuscular injection) to the hospital after injury. (2) A patient who is being subjected to mechanical ventilation. (3) A patient who has been genetically diagnosed with cystic fibrosis.

In addition to PcrV antibodies and antibody fragments, small molecule peptidomimetics or non-peptide mimetics can be designed to mimic the action of the PcrV antibodies in inhibiting or modulating *Pseudomonas* infection, presumably by interfering with the action of PcrV. Methods for designing such small molecule mimics are well known (see, for example, Ripka and Rich, *Curr. Opin. Chem. Biol.* 2:441-452, 1998; Huang, et al., *Biopolymers* 43:367-382, 1997; al-Obeidi, et al., *Mol. Biotechnol.* 9:205-223, 1998). Small molecule inhibitors that are designed based on the PcrV antibody may be screened for the ability to interfere with the PcrV-PcrV antibody binding interaction. Candidate small molecules exhibiting activity in such an assay may be optimized by methods that are well known in the art, including for example, in vitro screening assays, and further refined in in vivo assays for inhibition or modulation of *Pseudomonas* infection by any of the methods described herein or as are well known in the art. Such small molecule inhibitors of PcrV action should be useful in the present method for inhibiting or modulating a *Pseudomonas* infection.

In another aspect of the present invention, PcrV protein may be used to identify a PcrV receptor which may be present in the host cells, particularly in human cells, more particularly in human epithelial cells or macrophages. Identification of a PcrV receptor allows for the screening of small molecule libraries, for example combinatorial libraries, for candidates that interfere with PcrV binding. Such molecules may also be useful in a method to inhibit or modulate a *Pseudomonas* infection.

Our first attempts at receptor identification will be to use PcrV in pull-down experiments. PcrV will be fused to glutathione S-transferase (GST) and attached to column matrix for affinity chromatography of solubilized cellular extracts. Proteins binding specifically to PcrV will be eluted and subjected to amino terminal sequencing for identification. In parallel experiments PcrV will be subjected to yeast two-hybrid analysis. In this case PcrV is fused in frame with the DNA binding domain of Gal4. Once the clone is obtained it will be transformed into a suitable yeast host strain. The yeast strain containing the Gal4PcrV construct will be transformed with a Hela cell cDNA bank cloned in frame with the Gal4 activation domain. Double transformants that complement the ability to utilize histidine and produce beta galactosidase (proteins that interact with PcrV) will be analyzed genetically and at the nucleotide sequence level. In case the receptor is a cellular glycolipid we will utilize an overlay technique where glycolipids are separated by thin-layer chromatography and then probed with radiolabeled bacteria. The binding to specific components will be monitored by autoradiography. Similarly, epithelial and macrophage proteins will be separated by SDS-PAGE, blotted onto nitrocellulose and overlaid with radiolabeled bacteria or labeled PcrV. Again, the protein components to which the bacteria bind are then identified by autoradiography.

*Pseudomonas* species are known to infect a wide spectrum of hosts within the animal kingdom and even within the plant kingdom. As will be apparent to one of ordinary skill in the art, the compositions and methods disclosed herein may have use across a wide range of organisms in inhibiting or modulating diseases or conditions resulting from infection by a *Pseudomonas* species. The compositions and methods of the present invention are described herein particularly for application to *Pseudomonas aeruginosa* but it is well within the competence of one of ordinary skill in the art to apply the methods taught herein to other species.

EXAMPLES

1. Role of PcrV in Cytotoxicity

To determine the role of PcrV in type III-mediated regulation/secretion, we constructed a nonpolar allele of PcrV and used the construct to replace the wild-type allele in *P. aeruginosa* strain PA103, a strain that is highly cytotoxic in vitro (3) and causes lung epithelial damage in vivo (12, 13). Cytotoxicity and lung injury are due to the production of a specific cytotoxin, ExoU (3).

PA103ΔpcrV was characterized by the expression of several extracellular products that are secreted by the *P. aeruginosa* type III system which include the ExoU cytotoxin (3), PcrV (5), and a protein required for the translocation of toxins, PopD (14). SDS-polyacrylamide gel electrophoresis of concentrated culture supernatants indicated that the parental strain, PA103 is induced for production and secretion of the type III proteins by growth in medium containing a chelator of calcium, nitrilotriacetic acid (NTA) (FIG. 1). When an expression clone encoding PcrV was provided in trans in the parental strain, extracellular protein production in response to the presence or absence of NTA is normal. PA103ΔpcrV exhibits a calcium blind phenotype; extracellular protein production is strongly induced in both the presence and absence of NTA. These results suggest that the secretory system is fully functional but deregulated. This deregulated phenotype is in contrast to the calcium independent phenotype reported for an LcrV defective strain which fails to produce the extracellular Yops, grows at 37° C. regardless of the presence or absence of calcium, and shows only partial induction of the Yops (7). Complementing PA103ΔpcrV with a clone expressing wild-type PcrV restored normal regulation of extracellular protein production in response to NTA induction.

To test the contribution of PcrV to *P. aeruginosa* pathogenesis, two infection models were used. In an in vitro model the parental and several mutant derivative strains were compared for their ability to cause cytotoxicity in a CHO cell infection assay (3). The negative controls in this experiment included PA103popD::Ω, which has been previously shown to be defective in the translocation of type III virulence determinants (14) and PA103ΔexoU, which is non-cytotoxic due to the absence of ExoU production (3, 15).

After a 3 hour infection, CHO cells were unable to exclude trypan blue with the wild-type and ΔpcrV strain complemented with a plasmid construct expressing PcrV. Staining did not occur when CHO cells were infected with the negative control strains or with PA103ΔpcrV (data not shown). These results suggest that PcrV expression is required for cytotoxicity. Purified recombinant PcrV was not cytotoxic when added exogenously to tissue culture cells. Since secretion of the type III proteins required for translocation was unaffected by the deletion of pcrv (FIGS. 1A and B), PA103ΔpcrV appears to be defective in ExoU translocation.

FIGS. 1A and 1B are a stained gel (FIG. 1A) and Western blot (FIG. 1B) illustrating the phenotypic analysis of PA103ΔpcrV. The parental and ΔpcrV derivatives, with and without a plasmid expressing PcrV in trans, were grown in the absence or presence of the inducer of type III secretion in *P. aeruginosa*, nitrilotriacetic acid (NTA). The extracellular protein profile (FIG. 1A) was analyzed on a SDS-polyacrylamide gel (10%) stained with Coomassie blue. The migration of the *P. aeruginosa*-encoded type III proteins is indicated to the left and the migration of molecular weight markers is indicated on the right. FIG. 1B is a Western blot of a duplicate gel using antibodies specific for ExoU, PcrV, and PopD and $^{125}$I-Protein A to detect bound IgG.

Figure 2:
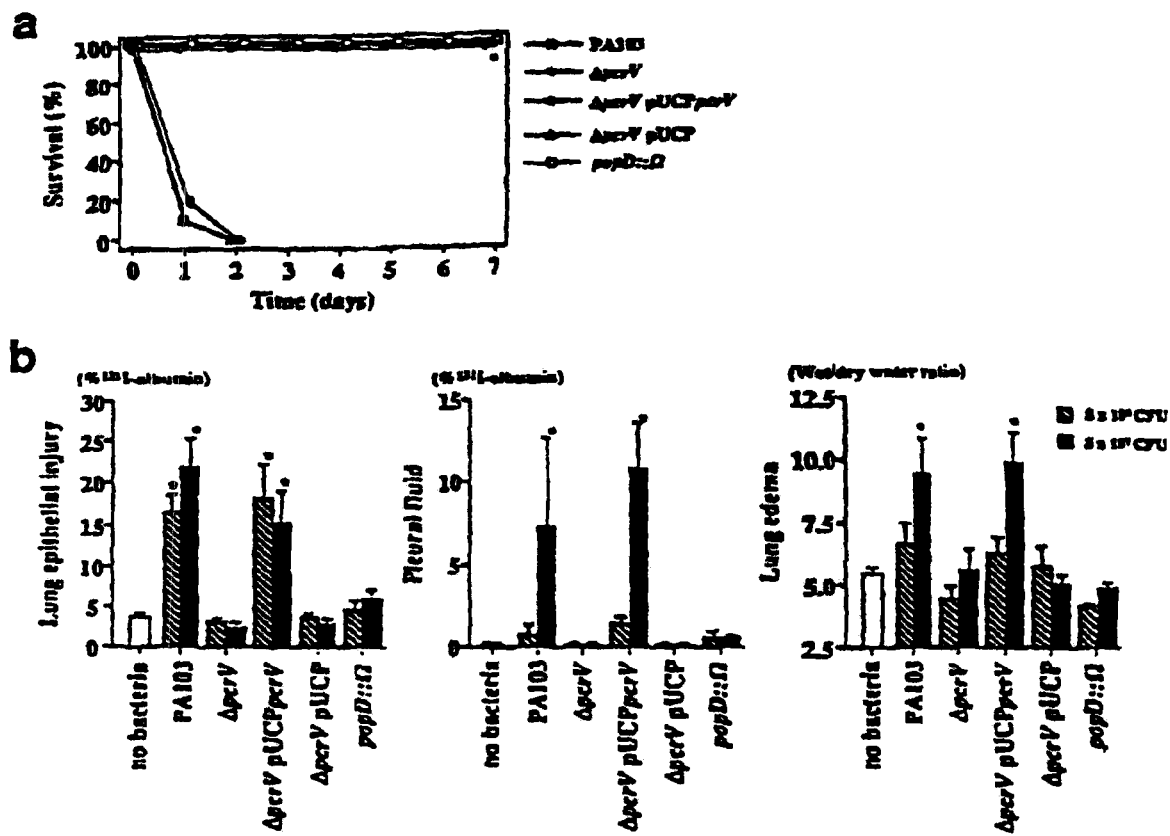
FIGS. 2A and 2B are a graph (FIG. 2A) and set of bar graphs (FIG. 2B) illustrating the survival and lung injury of *P. aeruginosa* parental and mutant strains.

Wild-type and mutant *P. aeruginosa* strains were tested in an acute lung infection model using low and high challenge doses of bacteria. Survival measurements indicated that PcrV and PopD were required to induce a lethal infection (FIG. 2A). In experiments utilizing three independent measurements of lung injury (the flux of labeled albumin from the airspaces of the lung to the bloodstream, the flux of labeled albumin from the airspaces of the lung to the pleural fluids, and the wet/dry ratio, which measures lung edema) the degree of injury caused by PA103ΔpcrV, the vector control strain (PA103 PA103ΔpcrV pUCP18), and PA103popD::Ω were no different than the uninfected control animals (FIG. 2B). Complementation of PA103ΔpcrV with pcrV in trans restored lung injury levels to those measured with the parental strain, PA103. Taken together these data indicate that PcrV expression is required for virulence of *P. aeruginosa* in the acute lung infection model and that part of the function of PcrV appears to be linked to the ability to translocate type III effector proteins into eukaryotic cells.

FIGS. 2A and 2B are a graph (FIG. 2A) and set of bar graphs (FIG. 2B) illustrating the survival and lung injury of *P. aeruginosa* parental and mutant strains. Referring to FIG. 2A, mice were challenged with $5 \times 10^5$ cfu of each of the indicated strains and survival was monitored for one week. Referring to FIG. 2B, lung injury was assessed by the flux of labeled albumin from the airspaces of the lung to the blood (lung epithelial injury), to the pleural fluid (pleural fluid) or by measuring the wet/dry ratio (lung edema). Two bacterial infectious doses were used as denoted by the solid and striped bars. Significant differences (*$p<0.001$) between control and test groups was determined by one-way ANOVA and Dunnet multiple comparison tests. The following abbreviations were used: PA103, parental wild-type strain; ΔpcrV, PA103ΔpcrV; ΔpcrVpUCPpcrV, PA103ΔpcrV complemented with a plasmid expressing PcrV; ΔpcrVpUCP, PA103ΔpcrV with a vector control; popD::Ω, PA103popD::Ω, a translocation defective strain.

2. Immunization with PcrV

Figure 3:
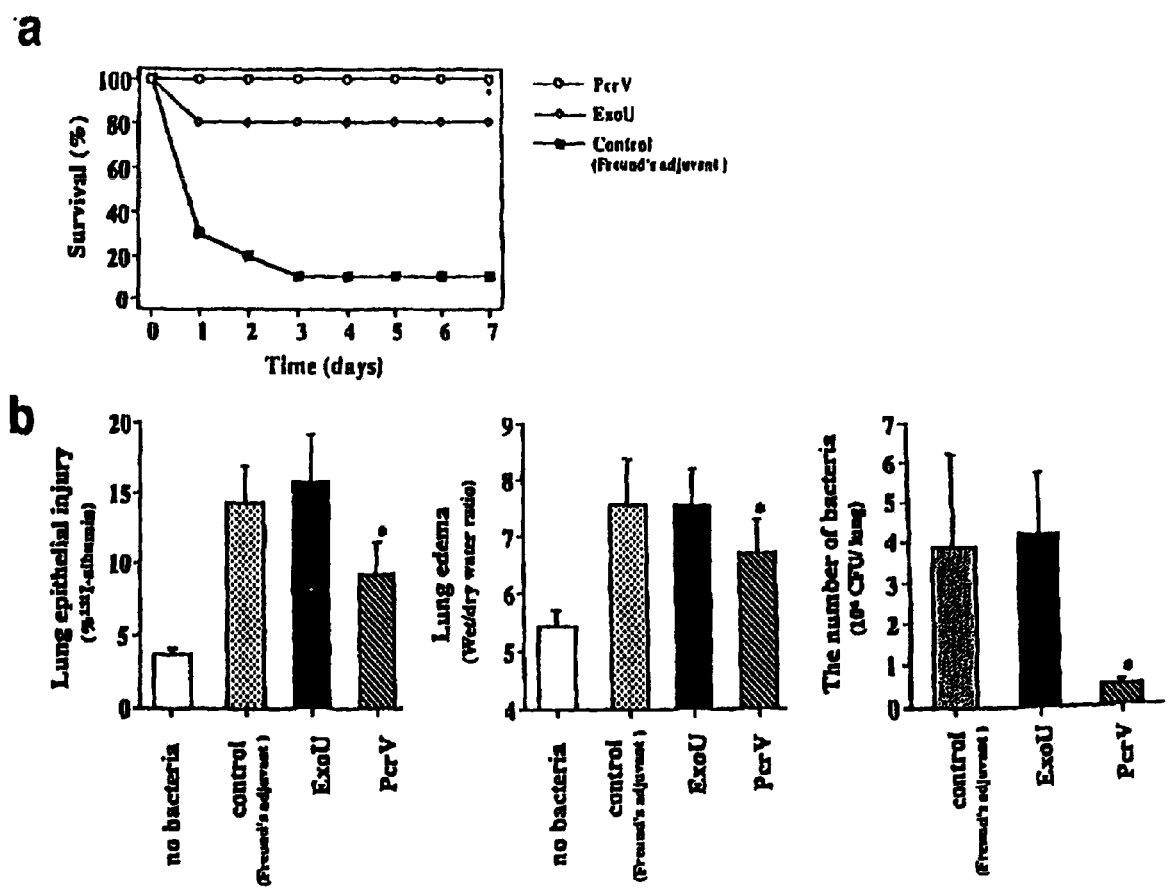
FIGS. 3A and 3B are a graph (FIG. 3A) and a set of bar graphs (FIG. 3B) illustrating the effect of immunization on survival, lung injury, and bacterial colonization.

To determine whether immunization with PcrV protected animals from a lethal lung infection, recombinant PcrV (rPcrV) or ExoU (rExoU) were purified as histidine-tagged fusion proteins and used as antigens. Mice were immunized and subsequently challenged via their airspaces with a lethal dose of strain PA103. When survival was measured, both vaccines protected the mice (FIG. 3A). When lung injury was assessed, only PcrV vaccinated animals had significantly less epithelial damage and lung edema (FIG. 3B). Animals immunized with the PcrV vaccine also had significantly fewer bacteria in their lungs, suggesting that a blockade of the *Pseudomonas* V antigen may facilitate rapid clearance of bacteria from the lung, protecting the animals from severe epithelial injury (FIG. 3B).

FIGS. 3A and 3B are a graph (FIG. 3A) and a set of bar graphs (FIG. 3B) illustrating the effect of immunization on survival, lung injury, and bacterial colonization. Referring to FIG. 3A, mice were immunized (PcrV, n=10; ExoU, n=5; control, n=10) as indicated and challenged with strain PA103 at $5 \times 10^5$ CFU/animal. The percent of surviving animals was determined for one week; $p<0.05$ by the Mantel-Cox log rank test. Referring to FIG. 3B, lung injury assessment and bacterial colonization of vaccinated animals 4 hours after installation of PA103. Lung epithelial injury, lung edema, and bacterial burden; PcrV, n=9; ExoU, n=4; and control, n=8. The final number of bacteria in the lung is indicated as the number on the Y axis $\times 10^4$ CFU. Significant differences (*) for lung injury ($p<0.01$), lung edema ($p<0.05$), and bacterial numbers ($p<0.05$) as determined by Dunnet multiple comparison test. One-way ANOVA for lung injury, $p=0.0005$; lung edema, $p=0.0437$; bacterial burden, $p=0.0075$.

Figure 4:
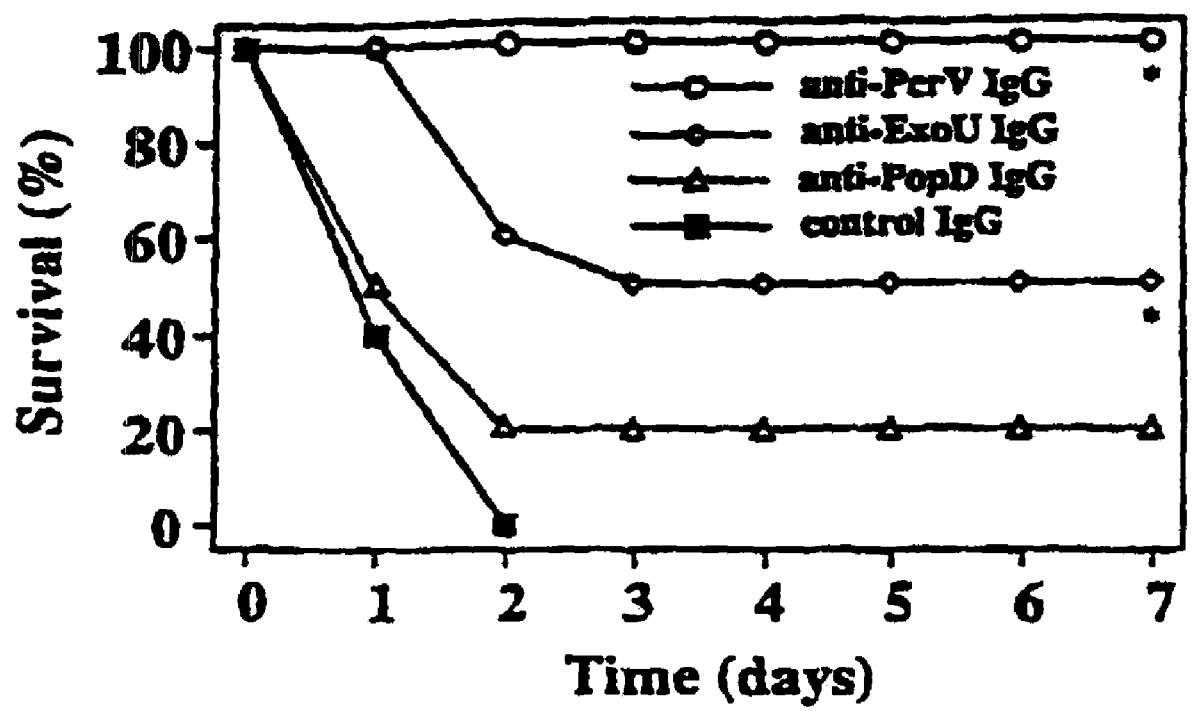
FIG. 4 is a graph of the number of animals surviving a challenge with $5 \times 10^5$ CFU/mouse of strain PA103 after passive administration of polyclonal IgG specific for PcrV, ExoU, PopD or control IgG from an unimmunized animal.

To determine whether therapeutic intervention was possible, mice were passively immunized with preimmune rabbit IgG or rabbit IgG specific for rPcrV, rExoU, or rPopD one hour prior to airspace instillation of PA103 at a concentration of $5 \times 10^5$ CFU/mouse. Antibodies to rPcrV provided complete protection to a lethal infection (FIG. 4). Anti-rExoU IgG provided partial survival, which was significantly different from the administration of control IgG, although all the surviving animals appeared severely ill during the trial. Survival was not improved by the passive transfer of antibodies to another of the type III translocation proteins, PopD. From these results we conclude that antibodies to PcrV are highly protective in the acute lung infection model and that PcrV may be exposed on the bacterial surface or in a soluble form that is available for antibody-antigen interactions.

FIG. 4 is a graph of the number of animals surviving a challenge with $5 \times 10^5$ CFU/mouse of strain PA103. Animals were pretreated with 100 ug of immune IgG or control IgG from an unimmunized rabbit (rPcrV, preimmune serum). N=10 for each group; *$p<0.05$ versus control group for treatment with anti-PcrV and anti-ExoU IgG preparations by Mantel-Cox log rank test.

If PcrV is accessible for neutralization, then concomitant administration of the bacterial inoculum with anti-rPcrV IgG should completely protect against lung injury and lethality. IgG preparations were mixed with the inoculum (10-fold higher dose than the lethal inoculum) prior to instillation of the bacteria into the lung and survival was measured. Only anti-rPcrV IgG was protective against this extreme infection (FIG. 5A). Lung injury was measured in animals infected with the normal lethal dose of $5 \times 10^5$ bacteria. The efflux of labeled albumin from the airspaces of the lung was only 3% more than uninfected controls (FIG. 5B) after co-administration of anti-rPcrV IgG. The decreased efflux of labeled protein from the lung to the pleural fluids was the same as the uninfected controls when anti-PcrV was included with the inoculum. Curiously lung edema, as measured by the wet/dry ratio, was significantly reduced by the addition of either anti-rPcrV or anti-rPopD. (FIG. 5B). Thus, the concomitant administration of anti-rPcrV IgG with the bacteria was even more effective in normalizing all the lung injury parameters than vaccination. These data support the accessibility of PcrV for antibody-mediated neutralization and document a clinically relevant decrease in lung injury; antibodies to PcrV may serve as therapeutic reagents in the treatment of severe nosocomial pneumonia caused by *Pseudomonas aeruginosa*.

Figure 5:
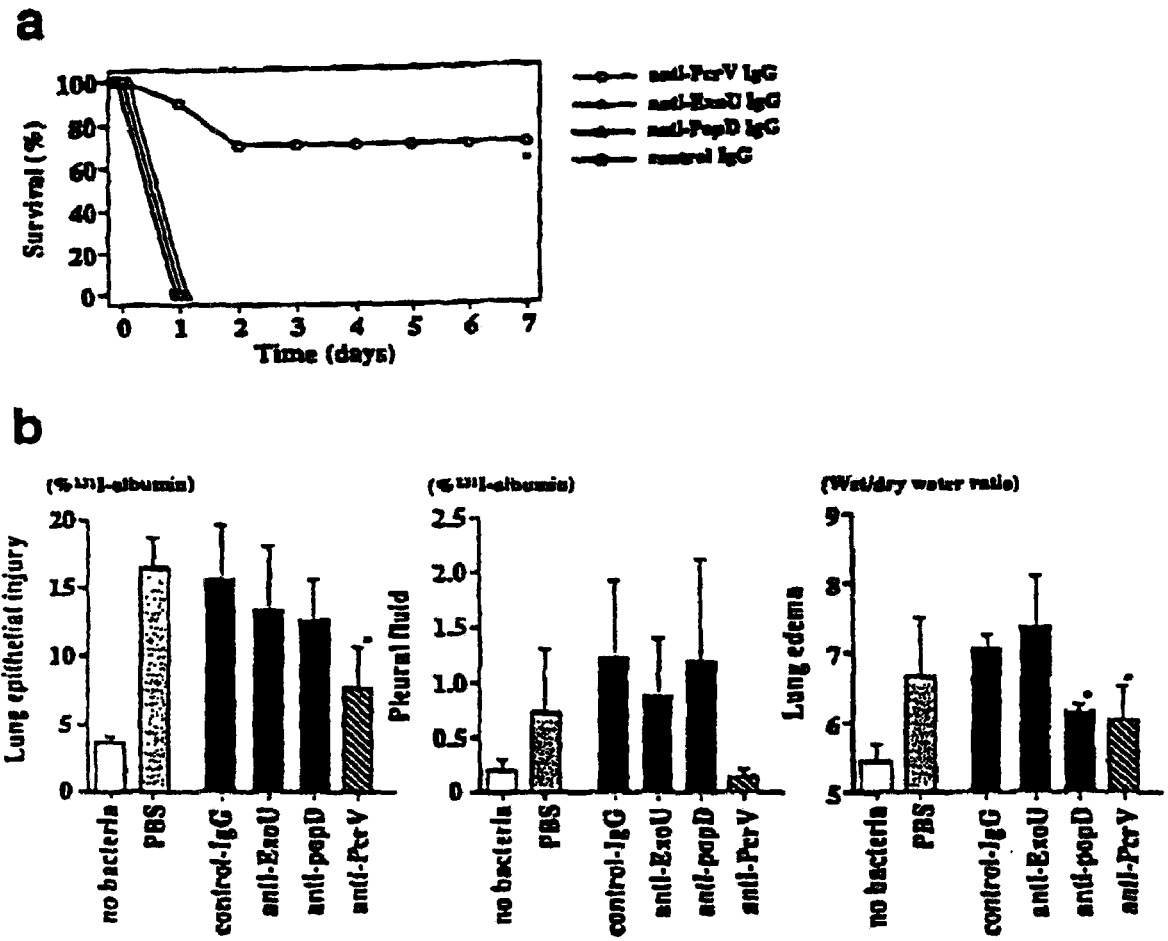
FIG. 5 is a graph (FIG. 5A) and a set of bar graphs (FIG. 5B) illustrating survival and protection from lung injury by concomitant administration of IgG to different bacterial antigens and bacterial challenge. One-way ANOVA for lung injury, $p=0.026$, and lung edema, $p<0.0005$.

FIG. 5 is a graph (FIG. 5A) and a set of bar graphs (FIG. 5B) illustrating survival and protection from lung injury by concomitant administration of IgG and bacterial challenge. IgG (5 ug) was mixed with either $5 \times 10^6$ (for survival assays, n=10 per group) or $5 \times 10^5$ (for the measurement of lung injury, n=4 to 6 animals per group) *P. aeruginosa* strain PA103. This mixture was instilled into the lungs and survival (FIG. 5A) or lung injury (FIG. 5B) was assessed. For survival, *$p<0.05$ versus control IgG for anti-PcrV by the Mantel-Cox log rank test; for lung epithelial injury and lung edema *$p<0.05$ versus control IgG by Dunnet multiple comparison test. One-way ANOVA for lung injury, $p=0.026$, and lung edema, $p<0.0005$.

In acute *P. aeruginosa* infections, the net effect of type III-mediated intoxication may be to promote the dissemination of the bacterium beyond the epithelium leading to infection of the pleural fluids, spleen, liver, and bloodstream. Blood-borne infections with *P. aeruginosa* from either acute ventilator-associated pneumonia or from burn wound infections can result in a 40-80% mortality rate in spite of aggressive antibiotic treatment (16). PcrV must be a component of the type III translocation complex in *P. aeruginosa*, as mutants defective in the production of this protein are unable to intoxicate CHO cells or cause lung epithelial injury even though they are able to produce and secrete the type III effectors and proteins required for translocation. Unlike PopD, which is also necessary for translocation, PcrV is accessible for antibody-mediated neutralization suggesting that antibodies may be useful therapeutic agents in acute infections.

3. Methods for Examples 1 and 2

Construction of a nonpolar insertion in PcrV and complementation. A 5.0-kb EcoRI-NsiI restriction fragment encoding pcrGVHpopBD and flanking sequences was cloned into the allelic replacement vector pNOT19 (17). Two NotI sites (one within pcrG and one within popB) were removed from the inserted sequences by using the Sculptor mutagenesis system (Amersham).

An internal SstI restriction fragment was deleted from pcrV, resulting in an in-frame deletion of residues 17-221 (pNOTΔpcrV). To select for integration of the plasmid, a gene encoding tetracycline resistance (TcΩ) was cloned into the HindIII site of the vector (pNOTΩΔpcrV). The MOB cassette (17) was added as a NotI fragment. Selection of merodiploids, resolution of plasmid sequences, and confirmation of allelic replacement was performed as previously described (18). A shuttle plasmid (pUCP, 19) was used to construct a clone to complement the pcrV deletion. The coding sequence for PcrV was amplified and cloned behind the control of the ExoS promoter region (20). The transcription of ExoS is coordinately regulated with the operons that control type III secretion and translocation in *P. aeruginosa* (2). The nucleotide sequence was confirmed for each DNA construct involving site specific mutagenesis, PCR amplification, or in-frame deletion.

SDS-PAGE and Western blot analysis of secreted products. *P. aeruginosa* were grown under inducing (+NTA) or non-inducing conditions (-NTA) for expression of the type III secreted products (18). Cultures were harvested based on optical density measurements at 540 nm and supernatant fractions were concentrated by the addition of a saturated solution of ammonium sulfate to a final concentration of 55%. Each lane of an SDS-polyacrylamide gel (11%) was loaded with 3 pi of a 20-fold concentrated supernatant and stained with Coomassie blue. An identical gel was subjected to Western blot analysis as previously described (3-5) using a cocktail of rabbit antisera, which specifically recognizes ExoU, PopD, and PcrV. Protein A labeled with $^{125}$I was used as a secondary reagent to identify bound IgG.

Infection models and lung injury assessments. Chinese Hamster Ovary cells (CHO) were used in an in vitro infection model designed to measure cytotoxicity and type III translocation (21). Briefly, a bacterial inoculum was prepared in tissue culture medium without serum. CHO cells, which were propagated in serum containing medium, were washed and infected with various *P. aeruginosa* strains at a multiplicity of infection of 5:1. Cultures were incubated under tissue culture conditions for 3 hours (37° C., 5% $CO_2$), washed, and stained with trypan blue. Permeability to the dye was determined from phase contrast photographs. Infection with the parental strain PA103, which expresses ExoU, results in trypan blue staining of approximately 80% of the monolayer after 3 hours of incubation and complete destruction of the monolayer at 4-5 hours of incubation. Mouse infections and assessment of lung injury was performed as previously described (16). Briefly, male 8- to 12-week old pathogen-free BALB/c mice were purchased from Simonsen Laboratories (Gilroy, Calif.) and housed in barrier conditions. The mice were briefly anesthetized with inhaled Metofane (methoxyflurane, Pitman-Moore, Mundelein, Ill.) and placed supine, at an angle of approximately 30°. Fifty microliters of the bacterial inoculum was instilled slowly into the left lobe using a modified 24 gauge animal feeding needle (Popper & Sons, Inc., New Hyde Park, N.Y.) inserted into the trachea via the oropharynx. When lung injury assessments were measured, 0.5 µCi of $^{131}$I-labeled human serum albumin (Merck-Frosst, Quebec, Canada), 0.05 µg of anhydrous Evans blue in ml of Ringer's lactate with 5% mouse albumin were added to the instillate. After 4 hours of infection, the mice were anesthetized, blood was collected by a carotid arterial puncture and median sternotomies were performed. The lungs, pleural fluids, tracheas, oropharynxes, stomachs, and livers were harvested, and the radioactivity was measured. The percentage of radioactive albumin that left the instilled lungs and entered the circulation or the pleural fluid was calculated by multiplying the counts measured in the terminal blood samples (per ml) times the blood volume (body weight×0.07). The wet-dry ratios of the lungs were determined by adding 1 ml of water to the lungs and homogenizing the mixture. Homogenates were placed in preweighed aluminum pans and dried to constant weight in an 80° C. oven for three days. Lung homogenates were also sequentially diluted and plated on sheep blood agar for quantitative assessment of bacteria.

Production of rabbit antiserum to PcrV, PopD, and ExoU. rPcrV, rPopD, and rExoU were produced as histidine tagged fusion proteins in pET16b and purified by nickel chromatography as previously described (22). Rabbits were injected intradermally (10 sites) with 300 µg of recombinant protein emulsified in Freund's complete adjuvant, boosted with antigen in Freund's incomplete adjuvant, and periodically bled at 7 day intervals. For passive immunization, the IgG fraction was isolated using Protein A column chromatography (Pierce Chemicals, Rockford, Ill.). Mice were injected with 100 µg IgG (intraperitoneal injection) 1 hour before challenge with $5\times10^5$ CFU of strain PA103. For active immunization with rPcrV and rExoU, endotoxin was removed from protein preparations by extraction with 1% Triton X-114 (23). Following the extractions, Triton X-114 was removed by Sephacryl S-200 chromatography. All vaccine preparations contained less than 1 ng of endotoxin per 40 µg of recombinant protein as determined by using a *limulus* amebocyte lysate assay (BioWhittaker, Walkersville, Md.). BALB/c mice were injected subcutaneously with 10 µg of recombinant proteins in Freund's complete adjuvant. At day 30 the mice were boosted with an additional 10 µg of antigen in Freund's incomplete adjuvant. On day 51 the mice were challenged by instillation of *P. aeruginosa* into their left lungs.

4. Synthesis of Monoclonal Antibodies

Mice were immunized with 10 µg of purified, LPS-free, recombinant PcrV in Freund's complete adjuvant and boosted two weeks later with the same dose of antigen emulsified in Freund's incomplete adjuvant. Immunizations were performed subcutaneous Spleens were harvested from mice one week after booster doses of PcrV in Freund's incomplete adjuvant.

A single spleen was placed in 5 ml of tissue culture medium without serum, cut into pieces and gently homogenized. Large pieces of tissue were allowed to settle from the homogenate and the supernatant, single-cell suspension was removed and subjected to centrifugation at 1200 rpm for 10 minutes. The pelleted cells were resuspended in 10 ml of a solution to lyse red blood cells for 5 minutes and subsequently underlaid with 10 ml of fetal bovine serum. The material was centrifuged at 1200 rpm for 8 minutes, the supernatant was discarded and the cells were suspended in 30 ml of medium.

Spleenic cells and myeloma cells (P3x63Ag8.653) were harvested by centrifugation at 1200 rpm for 10 minutes, and each pellet was separately suspended in 10 ml of tissue culture medium. $10^8$ spleen cells and $2\times10^7$ myeloma cells were mixed and pelleted together by centrifugation at 1200 rpm for 6 minutes. The supernatant was removed by aspiration and 1 ml of 35% polyethylene glycol (PEG) was added. The cells were suspended in this solution gently and centrifuged at 1000 rpm for 3 minutes. In some experiments centrifugation was eliminated.

Exactly 8 minutes after the addition of PEG, 25 ml of medium was added and the cells were gently resuspended. Following a 5 minute 1200 rpm centrifugation step, the cell pellet was suspended at a density of $1\times10^6$ per ml in 30% conditioned medium and 70% complete medium (with serum). The cells were incubated overnight at 37° C. The next day the cells were harvested by centrifugation and suspended in 200 ml of 30% conditioned medium and 70% complete medium with hypoxanthine, aminopterin and thymidine (HAT).

Approximately 0.2 ml of this cell suspension was added per well to ten 96-well plates (12 ml per 96 well plate). The density of the remaining cells was adjusted to $2.5\times10^5$ per ml and the cells were plated in the 96 well format. Plates were screened microscopically for single colonies and supernatants were subsequently tested for antibody production by enzyme-linked immunosorbent assay using recombinant PcrV as the antigen. Clones producing antibodies reactive to PcrV were subcultured to larger culture dishes and then isotyped.

The binding of antibodies was tested in an enzyme linked immunosorbent assay using recombinant PcrV as the antigen (histidine-tagged protein) coating the wells. Monoclonal antibodies were also tested in Western blot reactions using a *P. aeruginosa* supernatant containing native PcrV without the histidine tag.

5. Identification of PcrV Antigen

We obtained about three hundred cell lines producing antibodies that bound the tagged PcrV. These initial cell lines were preserved in liquid nitrogen for safekeeping. All cell lines were passaged to isolate stable clones. In conjunction with isolating stable clones we developed in in vitro assay as a correlate for protection against intoxication in animal infection models.

The hybridomas that were stable to passage and still produced antibodies reactive to PcrV in ELISA (approximately 80 cell lines) were subsequently tested in a Fluorescence Activated Cell Sorter using the following techniques and assumptions: We reasoned that if antibody is blocking the type III intoxication system, then in the presence of a monoclonal that blocks, fewer cells will be killed by our toxins. We exposed cells to each of the 80 monoclonal antibodies, added toxic bacteria, incubated, and then added a dye that is only permeable to dead cell DNA (propidium iodide). Excess dye was washed away and the cells were harvested, fixed, and analyzed by FACS. Dead cells would be fluorescent since the dye leaked in and stained DNA in the nucleus.

We found that if the cells were incubated with rabbit polyclonal anti-PcrV, mouse polyclonal anti-PcrV, or mab166 and bacteria, fewer cells died than in controls with irrelevant polyclonal antibody (anti-PopD) or the other 78 monoclonal antibodies.

Mab 166 was specifically found to bind to the bacterially encoded type III-secreted factor termed PcrV. PcrV mediates the interaction of *P. aeruginosa* and lung cells to facilitate the translocation of bacterial toxins that cause cellular death. This reaction is postulated to eliminate lung cells that are involved in the innate immune response to *P. aeruginosa*. The killing of these cells leaves the host epithelium open for *P. aeruginosa* colonization and spread to the pleural fluids and bloodstream. *P. aeruginosa*-encoded antibiotic resistance makes effective treatment unlikely once the bacteria have entered the bloodstream.

The protection afforded by mab 166 pre- and post-bacterial instillation in animal models of acute lung infection with *P. aeruginosa* is significant. To design antibody treatment modalities for intervention in human *P. aeruginosa* infections it will be necessary to produce either a human monoclonal antibody or to immunize at risk patients with the protective epitope of PcrV defined by mab 166. The goal of the work described below is to define the amino acid sequence of PcrV bound by mab 166.

Results

We used a molecular genetic approach to define the amino acid residues bound by mab 166. PcrV possesses 294 amino acids. The approach consisted of deleting parts of the molecule at the nucleotide sequence level using the polymerase chain reaction. Each product was cloned into a protein expression vector in frame with a gene encoding the glutathione S transferase protein. This strategy ensured that deletions encoding small numbers of PcrV amino acids could be detected using Western or dot blot techniques. Control bacterial lysates encoding only glutathione S transferase showed no reactivity to either our anti-PcrV polyclonal or mab 166 monoclonal antibody.

A total of 66 (with one full-length PcrV expression plasmid) clones were constructed, expressed, and tested for reactivity to rabbit polyclonal anti-PcrV antisera. All but one clone bound to anti-PcrV rabbit antibody verifying that the expressed proteins were in-frame with PcrV. The one non-reactive clone was eliminated from the analysis. None of the C-terminal deletions (n=5 constructs) bound mab 166 suggesting that the epitope was in the C-terminal half of the protein. Only one of the N-terminal truncation proteins (n=8 constructs) encoding PcrV amino acids (aa) 139-294 bound to mab 166. This experiment verified our hypothesis that the mab 166 epitope was encoded by the carboxyl terminal half of the protein. The remaining 51 constructs encoded various internal deletions of the molecule. Binding analysis tabulated in Table 1, below, demonstrated that the smallest epitope recognized by mab 166 consists of aa 144-257 of PcrV.

TABLE 1

PcrV Epitope Mapping
All proteins are amino-terminal tagged GST-PcrV truncates

| Amino Acids | Binding to pAb | Binding to mAb 166 |
|---|---|---|
| 1-294 (full-length) | Yes | Yes |
| (C-term truncates) | | |
| 1-46 | yes | no |
| 1-76 | yes | no |
| 1-134 | yes | no |
| 1-172 | yes | no |
| 1-75 + 173-294 | yes | no |
| (N-term truncates) | | |
| 139-294 | yes | yes |
| 148-294 | yes | no |
| 159-294 | yes | no |
| 164-294 | yes | no |
| 194-294 | yes | no |
| 261-294 | yes | no |
| 269-294 | yes | no |
| 278-294 | yes | no |
| (internal fragments) | | |
| 139-191 | yes | no |
| 139-195 | yes | no |
| 139-234 | yes | no |
| 139-243 | yes | no |
| 139-256 | yes | no |
| 139-257 | yes | yes; weak |
| 139-258 | yes | yes |
| 139-259 | yes | yes |
| 139-260 | yes | yes |
| 139-261 | yes | yes |
| 139-262 | yes | yes |
| 139-263 | yes | yes |
| 139-264 | yes | yes |
| 139-265 | yes | yes |
| 139-266 | yes | yes |
| 139-274 | yes | yes |
| 139-281 | yes | yes |
| 140-266 | yes | yes |
| 141-266 | yes | yes |
| 142-266 | yes | yes |
| 143-266 | yes | yes |
| 144-266 | yes | yes |
| 145-266 | yes | no |
| 146-266 | yes | no |
| 147-266 | yes | no |
| 148-170 | no* | no |
| 148-202 | yes | no |
| 159-202 | yes | no |
| 159-209 | yes | no |
| 159-216 | yes | no |
| 159-226 | yes | no |
| 159-234 | yes | no |
| 164-234 | yes | no |
| 164-243 | yes | no |
| 164-256 | yes | no |
| 164-266 | yes | no |
| 164-275 | yes | no |
| 164-281 | yes | no |
| 194-234 | yes | no |
| 194-243 | yes | no |
| 194-256 | yes | no |
| 194-266 | yes | no |
| 194-275 | yes | no |
| 194-281 | yes | no |
| 141-258 | yes | yes; weak |
| 142-258 | NT** | yes |
| 143-258 | yes | yes |
| 144-258 | yes | yes |
| 141-257 | yes | yes |
| 142-257 | yes | yes |
| 143-257 | yes | yes |
| 144-257 | yes; weak | yes; weak |

Notes:
*Truncate 148-170 is the only one that is not recognized by the rabbit polyclonal control antibody.
**NT: Not tested due to an insufficient amount of bacterial lysate.
As predicted, pGEX-4T-2 vector control lysates were not recognized by either antibody.
The smallest epitope of PcrV recognizable by mAb166 appears to consist of amino acids 144-257.

6. Examination of PcrV-Specific Antibody

Methods:

Poly A+ RNA extraction: Hybridoma cell line ml66 was cultured in complete Dulbeccos minimum essential medium with 4.5 g/L D-glucose, 10 mM HEPES, 50 µM 2-mercapto-ethanol, 3 mM L-glutamine, and 10% heat-inactivated fetal calf serum, 100 U/mL penicillin and 100 µg/mL streptomycin sulfate. After the cells reached confluent state in a 75 cm$^2$ flask, the cells were harvested from centrifuging at 600 rpm for 5 minutes. The pellet of the cells was homogenized in 2 mL of TRIzol reagent (Life Technologies, Gaithersburg, Md.), and total RNA (100 pg) was extracted after chloroform fractionation, isopropanol precipitation and 70% ethanol wash. Poly A+ RNA (4 µg) was extracted with oligotex mRNA spin-column (Qiagen, Valencia, Calif.).

RNA oligo-capping: mRNA (250 ng) was incubated with calf intestinal phosphatase at 50° C. for 1 hour to dephosphorylate non-mRNA or truncated mRNA. After the reaction, phenol/chloroform extraction and ethanol precipitation was performed and the dephosphorylated RNA was incubated with tobacco acid pyrophosphatase at 37° C. for 1 hour to remove the 5'-cap structure from full-length mRNA. After phenol/chloroform extractions and ethanol precipitation, the synthetic RNA oligo (GeneRacer RNA Oligo, Invitrogen, Carlsbad, Calif.) was ligated to the decapped RNA with T4 RNA ligase at 37° C. for 1 hour. After phenol/chloroform extraction and ethanol precipitation, the RNA was suspended in 13 µL diethylpyrocarbonate-treated water.

Reverse-transcribing mRNA: The RNA-oligo ligated, full-length mRNA (13 µL) was reverse-transcribed with 54 base the pair primer containing a dT tail of 18 nucleotides (GeneRacer Oligo dT, Invitrogen), and Avian myeloblastosis virus reverse transcriptase at 42° C. for 1 hour in 20 µL reaction. After the reaction, the sample was diluted 4 times with sterile water.

Amplifying cDNA ends by polymerase chain reaction (PCR): One microliter of the cDNA was used for PCR. The 5' primer from the synthetic RNA oligo sequence (GeneRacer 5' Primer, Invitrogen) and the murine immunoglobulin gamma 2b chain CH1 region specific primer or the murine immuno-globulin kappa chain CL region specific primer were used. The cycling parameters used for the PCR reaction was; 1) 94°

C., 2 minutes, 1 cycle, 2) 94° C., 30 seconds and 72° C., 1 minute, 5 cycle, 3) 94° C., 30 seconds, 70° C., 30 seconds, and 72° C., 1 minutes, 5 cycle, 4) 94° C., 30 seconds, 68° C., 30 seconds, and 72° C., 1 minutes, 20 cycle, 5) 72° C., 10 minutes.

Subcloning and DNA sequencing: PCR products (the murine immunoglobulin gamma 2b chain CH1 region derived fragment and the murine immunoglobulin kappa chain CL region derived fragment) were subcloned into the PCRII vector (TOPO cloning, Invitrogen) and submitted to UCSF Molecular Bioresource Center to analyze the DNA sequence.

SEQ ID NO:1 is the DNA sequence of m166 heavy chain mRNA, SEQ ID NO:2 is the amino acid sequence of the m166 heavy chain (IgG II$^b$), SEQ ID NO:3 is the DNA sequence of the ml66 light chain mRNA, and SEQ ID NO:4 is the amino acid sequence of the m166 light chain. FIGS. 6A, 6B and 7 examine the sequences and supply more detail.

Commercial Implications

One could use the antibody sequence to produce recombinant single chain antibodies that may block PcrV and could also utilize the sequence in gene delivery experiments, where one would deliver eukaryotic vectors that will then lead to the production of single chain antibodies in animals for prolonged periods. Finally, the sequence could be utilized to humanize the murine monoclonal antibody to produce a product that can be utilized in human patient care. One of skill in the art would look to standard methods such as grafting the antigen binding complementarity determining regions (CDRs) from variable domains of rodent antibodies on to human variable domains in order to create a humanized antibody.

7. Single Chain Antibody Against PcrV a. Assembling a Single Chain Antibody:

VH gene and VL gene were multiplied by polymerase chain reaction (PCR) with specific primers for each gene. Multiplied VH and VL fragments were assembled with a linker by using PCR with primers. The assembled single chain antibody gene (scFv::m166:VH and VL genes with linker) was transferred into the cloning vector pCR4 Topo (Invitrogen, Carlsbad, Calif.). Then, the coding sequence of scFv::m166 was subcloned into the *E. coli* expression vector pBAD/gIII (Invitrogen) in LMG194 as the host *E. coli*.

b. Protein Induction and Purification:

For protein induction, in RM medium containing 0.2% glucose and 100 µg of ampicillin, the transformed *E. coli* was cultured overnight at 37° C. in an orbital shaker (200 rpm), and the next day, 5 mL of the cultured *E. coli* was transferred into 500 mL of the same medium and incubated for 3 hours at room temperature at 100 rpm. After L-arabinose was added at the concentration of 0.004%, the *E. coli* was cultured overnight. The third day, the protein was harvested from the periplasmic space of the *E. coli* by osmotic shock methods. The solution including osmotic shock derived periplasmic protein was dialyzed overnight against the lysis buffer. During the fourth day, the dialyzed solution was applied onto a nickel-NTA column to purify the hexahistidine-tagged single chain antibody. The eluted solution from the nickel column was dialyzed against phosphate buffered saline overnight. On the fifth day, the dialyzed solution was applied to a centrifuge concentrator to make a higher concentration of scFv:m166.

c. The Binding Test:

The purified single chain antibody (scF::m166) was tested by using an enzyme linked immunosorbent assay against recombinant PcrV and by immunoblot (western blot) against both recombinant PcrV protein and native PcrV of *P. aeruginosa* PA103.

The single chain antibody will allow us to humanize the antibody utilizing phage-display techniques and to improve affinity of the antibody using these techniques. The single chain antibody can be utilized as a diagnostic tool (for histology) but would not be utilized as a therapy. However, the gene for the single chain antibody can be utilized in gene therapy, so that animals would produce single-chain antibodies over an interval, which could lead to protection against *P. aeruginosa* infections.

8. References

1. Wiener-Kronish, J. P., Sawa, T., Kurahashi, K., Ohara, M., and Gropper, M. A., "Pulmonary edema associated with bacterial pneumonia," Pulmonary Edema (eds Matthay, M. A. and Ingbar, D. H.) pp. 247-267 (Marcel Dekker, Inc., New York, 1998).
2. Frank, D. W., "The exoenzyme S regulon of *Pseudomonas aeruginosa*," *Mol. Microbiol.* 26:621-629 (1997).
3. Finck-Barbançon, V., et al., "ExoU expression by *Pseudomonas aeruginosa* correlates with acute cytotoxicity and epithelial injury," *Mol. Microbiol.* 25:547-557 (1997).
4. Yahr, T. L., Goranson, J., and Frank, D. W., "Exoenzyme S of *Pseudomonas aeruginosa* is secreted by a type III pathway," *Mol. Microbiol.* 22:991-1003 (1996).
5. Yahr, T. L., Mende-Mueller, L. M., Friese, M. B., and Frank, D. W., "Identification of type III secreted products of the *Pseudomonas aeruginosa* exoenzyme S regulon," *J. Bacteriol.* 179:7165-7168 (1997).
6. Hueck, C. J., "Type III protein secretion systems in bacterial pathogens of animals and plants," *Microbiol. Mol. Biol. Rev.* 62:379-433 (1998).
7. Skrzypek, E. and Straley, S. C., "Differential effects of deletion in IcrV on secretion of V antigen, regulation of the low-$Ca^{2+}$ response, and virulence of *Yersinia pestis*," *J. Bacteriol.* 177:2530-2542 (1995).
8. Nakajima, R. and Brubaker, R. R., "Association between virulence of *Yersinia pestis* and suppression of gamma interferon and tumor necrosis factor alpha," *Infect. Immun.* 61:23-31 (1993).
9. Nakajima, R., Motin, V. L., and Brubaker, R. R., "Suppression of cytokines in mice by protein A-V antigen fusion peptide and restoration of synthesis by active immunization," *Infect. Immun.* 63:3021-3029 (1995).
10. Nedialkov, Y. A., Motin, V. L., and Brubaker, R. R., "Resistance to lipopolysaccharide mediated by the *Yersinia pestis* V antigen-polyhistidine fusion peptide: amplification of interleukin-10," *Infect. Immun.* 63:1196-1203 (1997).
11. Nilles, M. L., Fields, K. A., and Straley, S. C., "The V antigen of *Yersinia pestis* regulates Yop vectorial targeting as well as Yop secretion through effects on YopB and LcrG," *J. Bacteriol.* 180:3410-3420 (1998).
12. Kudoh, I., Wiener-Kronish, J. P., Hashimoto, S., Pittet, J.-F., and Frank, D. W., "Exoproduct secretions of *Pseudomonas aeruginosa* strains influence severity of alveolar epithelial injury," *Am. J. Physio.* 267:L551-L556 (1994).
13. Apodaca, G., et al., "Characterization of *Pseudomonas aeruginosa*-induced MDCK cell injury: glycosylation-defective host cells are resistant to bacterial killing," *Infect. Immun.* 63:1541-1551 (1995).
14. Yahr, T. L., Vallis, A. J., Hancock, M. K., Barbieri, J. T., and Frank, D. W., "ExoY, a novel adenylate cyclase secreted by the *Pseudomonas aeruginosa* type III system," *Proc. Natl. Acad. Sci. USA*, in press (1998).

15. Finck-Barbançon, V., Yahr, T. L., and Frank, D. W., "Identification and characterization of SpcU, a chaperone required for efficient secretion of the ExoU cytotoxin," *J. Bacteriol.*, in press (1998).
16. Sawa, T., Corry, D. B., Gropper, M. A., Ohara, M., Kurahashi, K., and Wiener-Kronish, J. P., "IL-10 improves lung injury and survival in *Pseudomonas aeruginosa* pneumonia," *J. Immunol.* 159:2858-2866 (1997).
17. Schweizer, H. P., "Allelic exchange in *Pseudomonas aeruginosa* using novel ColE1-type vectors and a family of cassettes containing a portable oriT and the counter-selectable *Bacillus subtilis* sacB marker," *Mol. Microbiol.* 6:1195-1204 (1992).
18. Frank, D. W., Nair, G., and Schweizer, H. P., "Construction and characterization of chromosomal insertional mutations of the *Pseudomonas aeruginosa* exoenzyme S trans-regulatory locus," *Infect. Immun.* 62:554-563 (1994).
19. Schweizer, H. P., "*Escherichia-Pseudomonas* shuttle vectors derived from pUC18/19," *Gene* 97:109-112 (1991).
20. Yahr, T. L., Hovey, A. K., Kulich, S. M., and Frank, D. W., "Transcriptional analysis of the *Pseudomonas aeruginosa* exoenzyme S structural gene," *J. Bacteriol.* 177:1169-1178 (1995).
21. Vallis, A. J., Yahr, T. L., Barbieri, J. T., and Frank, D. W., "Regulation of ExoS production by *Pseudomonas aeruginosa* in response to tissue culture conditions," *Infect. Immun.* submitted.
22. Yahr, T. L., Barbieri, J. T., and Frank, D. W., "Genetic relationship between the 53- and 49-kilodalton forms of exoenzyme S from *Pseudomonas aeruginosa*," *J. Bacteriol.* 178:1412-1419 (1996).
23. Aidi, Y. and Pabst, M. J., "Removal of endotoxin from protein solutions by phase separation using Triton X-114," *J. Immunol. Methods* 132:191-195 (1990).

We claim:

1. A method of diagnosing *Pseudomonas aeruginosa* infection comprising:
   (a) exposing a patient's sample to a nucleotide probe, wherein the probe hybridizes specifically to nucleotides between residues 626-1510 of SEQ ID NO:8 or nucleotides encoding amino acid residues 144-257 of SEQ ID NO: 7, and wherein the probe comprises a single nucleotide sequence consisting of at least forty contiguous nucleotides between residues 626-1510 of SEQ ID NO:8;
   (b) detecting the hybridization via PCR or RT-PCR with two primers, wherein each primer consists of a single nucleotide sequence consisting of at least 25 continuous nucleotides between residues 626-1510 of SEQ ID NO:8; and
   (c) correlating *Pseudomonas aeruginosa* infection with the presence of the hybridized probe.

2. A method of diagnosing *Pseudomonas aeruginosa* infection comprising:
   (a) exposing a patient's sample to a nucleotide probe, wherein the probe hybridizes specifically to nucleotides between residues 626-1510 of SEQ ID NO:8 or nucleotides encoding amino acid residues 144-257 of SEQ ID NO: 7, and wherein the probe comprises a single nucleotide sequence consisting of at least forty contiguous nucleotides between residues 626-1510 of SEQ ID NO:8;
   (b) detecting the hybridization via PCR or RT-PCR with a PCR primer consisting of a single nucleotide sequence consisting of at least 25 continuous nucleotides between residues 626-1510 of SEQ ID NO:8; and
   (c) correlating *Pseudomonas aeruginosa* infection with the presence of the hybridized probe.

* * * * *

SEQUENCE LISTING

<160> NUMBER OF SEQ ID NOS: 8

<210> SEQ ID NO 1
<211> LENGTH: 1588
<212> TYPE: DNA
<213> ORGANISM: Mus musculus

<400> SEQUENCE: 1

```
ccatcctctt ctcatagagc ctccatcaga gcatggctgt cttggggctg ctcttctgcc      60
tggtgacatt cccaagctgt gtcctatccc aggtgcagct gaagcagtca ggacctggcc     120
tagtgcagcc ctcacagagc ctgtccatca cctgcacagt ctctggtttc tcattaacta     180
gctatggtgt acactgggtt cgtcagtctc caggaaaggg tctggagtgg ctgggagtga     240
tatggagtgg tggagacaca gactataatg cagctttcat atccagactg agcatcagca     300
aggacaattc caagagccaa ctcttcttta aaatgaacag tctgcgagct actgacacag     360
ccatatatta ctgtgccaga aatagagggg atatttacta tgatttcact tatgccatgg     420
actactgggg tcaaggaacc tcagtcaccg tctcctcagc caaaacaaca cccccatcag     480
tctatccact ggccctgggt gtggagata caactggttc ctccgtgact ctgggatgcc     540
tggtcaaggg ctacttccct gagtcagtga ctgtgacttg gaactctgga tccctgtcca     600
gcagtgtgca caccttccca gctctcctgc agtctggact ctacactatg agcagctcag     660
tgactgtccc ctccagcacc tggccaagtc agaccgtcac ctgcagcgtt gctcacccag     720
ccagcagcac cacggtggac aaaaaacttg agcccagcgg gcccatttca acaatcaacc     780
cctgtcctcc atgcaaggag tgtcacaaat gcccagctcc taacctcgag ggtggaccat     840
ccgtcttcat cttccctcca aatatcaagg atgtactcat gatctccctg acacccaagg     900
tcacgtgtgt ggtggtggat gtgagcgagg atgacccaga cgtccagatc agctggtttg     960
tgaacaacgt ggaagtacac acagctcaga cacaaaccca tagagaggat tacaacagta    1020
ctatccgggt ggtcagcacc ctccccatcc agcaccagga ctggatgagt ggcaaggagt    1080
tcaaatgcaa ggtcaacaac aaagacctcc catcacccat cgagagaacc atctcaaaaa    1140
ttaaagggct agtcagagct ccacaagtat acatcttgcc gccaccagca gagcagttgt    1200
ccaggaaaga tgtcagtctc acttgcctgg tcgtgggctt caaccctgga gacatcagtg    1260
tggagtggac cagcaatggg catacagagg agaactacaa ggacaccgca ccagtcctgg    1320
actctgacgg ttcttacttc atatatagca agctcaatat gaaaacaagc aagtgggaga    1380
```

```
aaacagattc cttctcatgc aacgtgagac acgagggtct gaaaaattac tacctgaaga    1440
agaccatctc ccggtctccg ggtaaatgag ctcagcaccc acaaagctct caggtcctaa    1500
gagacactgg cacccatatc catgcatccc ttgtataaat aaagcatcca gcaaagcctg    1560
gtaccatgta aaaaaaaaaa aaaaaaaa                                       1588
```

<210> SEQ ID NO 2
<211> LENGTH: 478
<212> TYPE: PRT
<213> ORGANISM: Mus musculus

<400> SEQUENCE: 2

```
Met Ala Val Leu Gly Leu Leu Phe Cys Leu Val Thr Phe Pro Ser Cys
1               5                   10                  15

Val Leu Ser Gln Val Gln Leu Lys Gln Ser Gly Pro Gly Leu Val Gln
            20                  25                  30

Pro Ser Gln Ser Leu Ser Ile Thr Cys Thr Val Ser Gly Phe Ser Leu
        35                  40                  45

Thr Ser Tyr Gly Val His Trp Val Arg Gln Ser Pro Gly Lys Gly Leu
    50                  55                  60

Glu Trp Leu Gly Val Ile Trp Ser Gly Gly Asp Thr Asp Tyr Asn Ala
65                  70                  75                  80

Ala Phe Ile Ser Arg Leu Ser Ile Ser Lys Asp Asn Ser Lys Ser Gln
                85                  90                  95

Leu Phe Phe Lys Met Asn Ser Leu Arg Ala Thr Asp Thr Ala Ile Tyr
            100                 105                 110

Tyr Cys Ala Arg Asn Arg Gly Asp Ile Tyr Tyr Asp Phe Thr Tyr Ala
        115                 120                 125

Met Asp Tyr Trp Gly Gln Gly Thr Ser Val Thr Val Ser Ser Ala Lys
    130                 135                 140

Thr Thr Pro Pro Ser Val Tyr Pro Leu Ala Pro Gly Cys Gly Asp Thr
145                 150                 155                 160

Thr Gly Ser Ser Val Thr Leu Gly Cys Leu Val Lys Gly Tyr Phe Pro
                165                 170                 175

Glu Ser Val Thr Val Thr Trp Asn Ser Gly Ser Leu Ser Ser Ser Val
            180                 185                 190

His Thr Phe Pro Ala Leu Leu Gln Ser Gly Leu Tyr Thr Met Ser Ser
        195                 200                 205

Ser Val Thr Val Pro Ser Ser Thr Trp Pro Ser Gln Thr Val Thr Cys
    210                 215                 220

Ser Val Ala His Pro Ala Ser Ser Thr Thr Val Asp Lys Lys Leu Glu
225                 230                 235                 240

Pro Ser Gly Pro Ile Ser Thr Ile Asn Pro Cys Pro Pro Cys Lys Glu
                245                 250                 255

Cys His Lys Cys Pro Ala Pro Asn Leu Glu Gly Gly Pro Ser Val Phe
            260                 265                 270

Ile Phe Pro Pro Asn Ile Lys Asp Val Leu Met Ile Ser Leu Thr Pro
        275                 280                 285

Lys Val Thr Cys Val Val Val Asp Val Ser Glu Asp Asp Pro Asp Val
    290                 295                 300

Gln Ile Ser Trp Phe Val Asn Asn Val Glu Val His Thr Ala Gln Thr
305                 310                 315                 320

Gln Thr His Arg Glu Asp Tyr Asn Ser Thr Ile Arg Val Val Ser Thr
                325                 330                 335

Leu Pro Ile Gln His Gln Asp Trp Met Ser Gly Lys Glu Phe Lys Cys
```

```
                340             345             350
Lys Val Asn Asn Lys Asp Leu Pro Ser Pro Ile Glu Arg Thr Ile Ser
            355                 360                 365
Lys Ile Lys Gly Leu Val Arg Ala Pro Gln Val Tyr Ile Leu Pro Pro
        370                 375                 380
Pro Ala Glu Gln Leu Ser Arg Lys Asp Val Ser Leu Thr Cys Leu Val
385                 390                 395                 400
Val Gly Phe Asn Pro Gly Asp Ile Ser Val Glu Trp Thr Ser Asn Gly
                405                 410                 415
His Thr Glu Glu Asn Tyr Lys Asp Thr Ala Pro Val Leu Asp Ser Asp
            420                 425                 430
Gly Ser Tyr Phe Ile Tyr Ser Lys Leu Asn Met Lys Thr Ser Lys Trp
        435                 440                 445
Glu Lys Thr Asp Ser Phe Ser Cys Asn Val Arg His Glu Gly Leu Lys
        450                 455                 460
Asn Tyr Tyr Leu Lys Lys Thr Ile Ser Arg Ser Pro Gly Lys
465                 470                 475

<210> SEQ ID NO 3
<211> LENGTH: 979
<212> TYPE: DNA
<213> ORGANISM: Mus musculus

<400> SEQUENCE: 3 acacccttg ctggagtcag aatcacactg atcacacaca gtcatgagtg tgctcactca    60
ggtcctggcg ttgctgctgc tgtggcttac aggtgccaga tgtgacatcc agatgactca   120
gtctccagcc tccctatctg catctgtggg agaaactgtc accatcacat gtcgagcaag   180
tgggaatatt caaaattatt tagcatggta tcagcagaca cagggaaaat ctcctcagct   240
cctggtctat tctgcaaaaa ccttagcaga tggtgtgcca tcaaggttca gtggcagtgg   300
atcaggaaca caatattctc tcaagatcaa cagcctgcag cctgaagatt ttgggagtta   360
ttactgtcaa cattttgga gtactccgta cacgttcgga gggggaccga agctggaaat   420
aaaacgggct gatgctgcac caactgtatc catcttccca ccatccagtg agcagttaac   480
atctggaggt gcctcagtcg tgtgcttctt gaacaacttc taccccaaag acatcaatgt   540
caagtggaag attgatggca gtgaacgaca aaatggcgtc ctgaacagtt ggactgatca   600
ggacagcaaa gacagcacct acagcatgag cagcaccctc acgttgacca aggacgagta   660
tgaacgacat aacagctata cctgtgaggc cactcacaag acatcaactt cacccattgt   720
caagagcttc aacaggaatg agtgttagag acaaggtcc tgagacgcca ccaccagctc   780
cccagctcca tcctatcttc ccttctaagg tcttggaggc ttcccacaa gcgacctacc   840
actgttgcgg tgctccaaac ctcctcccca cctccttctc ctcctcctcc ctttccttgg   900
cttttatcat gctaatattt gcagaaaata ttcaataaag tgagtctttg caaaaaaaaa   960
aaaaaaaaa aaaaaaaa                                                   979

<210> SEQ ID NO 4
<211> LENGTH: 234
<212> TYPE: PRT
<213> ORGANISM: Mus musculus

<400> SEQUENCE: 4

Met Ser Val Leu Thr Gln Val Leu Ala Leu Leu Leu Leu Trp Leu Thr
1               5                   10                  15

Gly Ala Arg Cys Asp Ile Gln Met Thr Gln Ser Pro Ala Ser Leu Ser
```

```
                   20                  25                  30
Ala Ser Val Gly Glu Thr Val Thr Ile Thr Cys Arg Ala Ser Gly Asn
            35                  40                  45

Ile Gln Asn Tyr Leu Ala Trp Tyr Gln Gln Thr Gln Gly Lys Ser Pro
     50                  55                  60

Gln Leu Leu Val Tyr Ser Ala Lys Thr Leu Ala Asp Gly Val Pro Ser
65                  70                  75                  80

Arg Phe Ser Gly Ser Gly Ser Gly Thr Gln Tyr Ser Leu Lys Ile Asn
                85                  90                  95

Ser Leu Gln Pro Glu Asp Phe Gly Ser Tyr Tyr Cys Gln His Phe Trp
            100                 105                 110

Ser Thr Pro Tyr Thr Phe Gly Gly Gly Thr Lys Leu Glu Ile Lys Arg
        115                 120                 125

Ala Asp Ala Ala Pro Thr Val Ser Ile Phe Pro Pro Ser Ser Glu Gln
    130                 135                 140

Leu Thr Ser Gly Gly Ala Ser Val Val Cys Phe Leu Asn Asn Phe Tyr
145                 150                 155                 160

Pro Lys Asp Ile Asn Val Lys Trp Lys Ile Asp Gly Ser Glu Arg Gln
                165                 170                 175

Asn Gly Val Leu Asn Ser Trp Thr Asp Gln Asp Ser Lys Asp Ser Thr
            180                 185                 190

Tyr Ser Met Ser Ser Thr Leu Thr Leu Thr Lys Asp Glu Tyr Glu Arg
        195                 200                 205

His Asn Ser Tyr Thr Cys Glu Ala Thr His Lys Thr Ser Thr Ser Pro
    210                 215                 220

Ile Val Lys Ser Phe Asn Arg Asn Glu Cys
225                 230

<210> SEQ ID NO 5
<211> LENGTH: 882
<212> TYPE: DNA
<213> ORGANISM: Artificial Sequence
<220> FEATURE:
<223> OTHER INFORMATION: Synthetic oligonucleotide encoding a synthetic
      recombinant single-chain antibody

<400> SEQUENCE: 5
atgaaaaaac tgctgttcgc gattccgctg gtggtgccgt tctatagcca tagcaccatg      60
gagctcgagc ggcaggtgca gctgaagcag tcaggacctg gcctagtgcg gccctcacag     120
agcctgtcca tcacctgcac agtctctggt ttctcattaa ctagctatgg tgtacactgg     180
gttcgtcagt ctccaggaaa gggtctggag tggctgggag tgatatggag tggtggagac     240
acagactata atgcagcttt catatccaga ctgagcatca gcaaggacaa ttccaagagc     300
caactcttct ttaaaatgaa cagtctgcga gctactgaca cagccatata ttactgtgcc     360
agaaatagag gggatattta ctatgatttc acttatgcga tggactactg ggtcaagga     420 acctcagtca ccgtctcctc aggtggaggc ggctcaggcg aggtggctc tggcggtggc     480 ggatcggaca tccagatgac tcagtctcca gcctccctat ctgcatctgt gggagaaact     540
gtcaccatca catgtcgagc aagtgggaat attcaaaatt atttagcatg gtatcagcag     600
acacagggaa aatctcctca gctcctggtc tattctgcaa aaaccttagc agatggtgtg     660
ccatcaaggt tcagtggcag tggatcagga acacaatatt ctctcaagat caacagcctg     720
cagcctgaag attttgggag ttattactgt caacattttt ggagtactcc gtacacgttc     780
ggagggggga ccaagctgga aataaaacgg gctctagaac aaaaactcat ctcagaagag     840
```
gatctgaata gcgccgtcga ccatcatcat catcatcatt ga            882

<210> SEQ ID NO 6
<211> LENGTH: 293
<212> TYPE: PRT
<213> ORGANISM: Artificial Sequence
<220> FEATURE:
<223> OTHER INFORMATION: Synthetic construct

<400> SEQUENCE: 6

Met Lys Lys Leu Leu Phe Ala Ile Pro Leu Val Val Pro Phe Tyr Ser
1               5                   10                  15

His Ser Thr Met Glu Leu Glu Arg Gln Val Gln Leu Lys Gln Ser Gly
            20                  25                  30

Pro Gly Leu Val Arg Pro Ser Gln Ser Leu Ser Ile Thr Cys Thr Val
        35                  40                  45

Ser Gly Phe Ser Leu Thr Ser Tyr Gly Val His Trp Val Arg Gln Ser
    50                  55                  60

Pro Gly Lys Gly Leu Glu Trp Leu Gly Val Ile Trp Ser Gly Gly Asp
65                  70                  75                  80

Thr Asp Tyr Asn Ala Ala Phe Ile Ser Arg Leu Ser Ile Ser Lys Asp
                85                  90                  95

Asn Ser Lys Ser Gln Leu Phe Phe Lys Met Asn Ser Leu Arg Ala Thr
            100                 105                 110

Asp Thr Ala Ile Tyr Tyr Cys Ala Arg Asn Arg Gly Asp Ile Tyr Tyr
        115                 120                 125

Asp Phe Thr Tyr Ala Met Asp Tyr Trp Gly Gln Gly Thr Ser Val Thr
    130                 135                 140

Val Ser Ser Gly Gly Gly Gly Ser Gly Gly Gly Gly Ser Gly Gly Gly
145                 150                 155                 160

Gly Ser Asp Ile Gln Met Thr Gln Ser Pro Ala Ser Leu Ser Ala Ser
                165                 170                 175

Val Gly Glu Thr Val Thr Ile Thr Cys Arg Ala Ser Gly Asn Ile Gln
            180                 185                 190

Asn Tyr Leu Ala Trp Tyr Gln Gln Thr Gln Gly Lys Ser Pro Gln Leu
        195                 200                 205

Leu Val Tyr Ser Ala Lys Thr Leu Ala Asp Gly Val Pro Ser Arg Phe
    210                 215                 220

Ser Gly Ser Gly Ser Gly Thr Gln Tyr Ser Leu Lys Ile Asn Ser Leu
225                 230                 235                 240

Gln Pro Glu Asp Phe Gly Ser Tyr Tyr Cys Gln His Phe Trp Ser Thr
                245                 250                 255

Pro Tyr Thr Phe Gly Gly Gly Thr Lys Leu Glu Ile Lys Arg Ala Leu
            260                 265                 270

Glu Gln Lys Leu Ile Ser Glu Glu Asp Leu Asn Ser Ala Val Asp His
        275                 280                 285

His His His His
    290

<210> SEQ ID NO 7
<211> LENGTH: 294
<212> TYPE: PRT
<213> ORGANISM: Pseudomonas aeruginosa

<400> SEQUENCE: 7

Met Glu Val Arg Asn Leu Asn Ala Ala Arg Glu Leu Phe Leu Asp Glu
1               5                   10                  15

```
Leu Leu Ala Ala Ser Ala Ala Pro Ala Ser Ala Glu Gln Glu Leu
         20                  25                  30
Leu Ala Leu Arg Ser Glu Arg Ile Val Leu Ala His Ala Gly Gln
         35                  40                  45
Pro Leu Ser Glu Ala Gln Val Leu Lys Ala Leu Ala Trp Leu Leu Ala
 50                  55                  60
Ala Asn Pro Ser Ala Pro Pro Gly Gln Gly Leu Glu Val Leu Arg Glu
 65                  70                  75                  80
Val Leu Gln Ala Arg Arg Gln Pro Gly Ala Gln Trp Asp Leu Arg Glu
                 85                  90                  95
Phe Leu Val Ser Ala Tyr Phe Ser Leu His Gly Arg Leu Asp Glu Asp
                 100                 105                 110
Val Ile Gly Val Tyr Lys Asp Val Leu Gln Thr Gln Asp Gly Lys Arg
                 115                 120                 125
Lys Ala Leu Leu Asp Glu Leu Lys Ala Leu Thr Ala Glu Leu Lys Val
         130                 135                 140
Tyr Ser Val Ile Gln Ser Gln Ile Asn Ala Ala Leu Ser Ala Lys Gln
145                 150                 155                 160
Gly Ile Arg Ile Asp Ala Gly Gly Ile Asp Leu Val Asp Pro Thr Leu
                 165                 170                 175
Tyr Gly Tyr Ala Val Gly Asp Pro Arg Trp Lys Asp Ser Pro Glu Tyr
                 180                 185                 190
Ala Leu Leu Ser Asn Leu Asp Thr Phe Ser Gly Lys Leu Ser Ile Lys
         195                 200                 205
Asp Phe Leu Ser Gly Ser Pro Lys Gln Ser Gly Glu Leu Lys Gly Leu
 210                 215                 220
Ser Asp Glu Tyr Pro Phe Glu Lys Asp Asn Asn Pro Val Gly Asn Phe
225                 230                 235                 240
Ala Thr Thr Val Ser Asp Arg Ser Arg Pro Leu Asn Asp Lys Val Asn
                 245                 250                 255
Glu Lys Thr Thr Leu Leu Asn Asp Thr Ser Ser Arg Tyr Asn Ser Ala
                 260                 265                 270
Val Glu Ala Leu Asn Arg Phe Ile Gln Lys Tyr Asp Ser Val Leu Arg
         275                 280                 285
Asp Ile Leu Ser Ala Ile
         290

<210> SEQ ID NO 8
<211> LENGTH: 4168
<212> TYPE: DNA
<213> ORGANISM: Pseudomonas aeruginosa

<400> SEQUENCE: 8
ggtctggatc gtgatgttgc gtcggcggca ggcgcgcagc ggattggcca atccattcgc     60
cgcgctgtac ctgctggcgg aggccacgct cgatacgctg gaccgcgcc  agcgtctcta    120
cggcaaggtc ctggcgctgg ccggcagccc actgcctggc gagcgcatgg cgcgcttcta    180
tcgccgctgg accggcgccg ccgagcccgc cgacggctgg ttcgagctgg aggccgggcg    240
ggtggtgacg cagcgaagcc tgcgaaaacg acaaaaaccc gaccgtgcct gacaggctcc    300
ggcaacgtcg atccctacca tgggcgacat gaacgaatac accgaagaca ccctgcgggc    360
gaccgtccag gccgccgaac tggcgattcg cgacagcgag gaacgcggcc gcctgctggc    420
ggaaatgtgg caaggcctgg gtttgccgc ggacgccggc gagctgctgt tccaggcgcc    480
ggagcgagag ctggcgcgag ccgccgaaga ggagctgctg gccgaactgc ggcgcatgcg    540
```

```
cagttcccag ccgacgcagg gcgagcaggg tacccggccg cggcgtccga cgccgatgcg    600
tggcttgttg atctgaggaa tcacgatgga agtcagaaac cttaatgccg ctcgcgagct    660
gttcctggac gagctcctgg ccgcgtcggc ggcgcctgcc agtgccgagc aggaggaact    720
gctggccctg ttgcgcagcg agcggatcgt gctggcccac gccggccagc cgctgagcga    780
ggcgcaagtg ctcaaggcgc tcgcctggtt gctcgcggcc aatccgtccg cgcctccggg    840
gcagggcctc gaggtactcc gcgaagtcct gcaggcacgt cggcagcccg gtgcgcagtg    900
ggatctgcgc gagttcctgg tgtcggccta tttcagcctg cacgggcgtc tcgacgagga    960
tgtcatcggt gtctacaagg atgtcctgca gacccaggac ggcaagcgca aggcgctgct   1020
cgacgagctc aaggcgctga ccgcggagtt gaaggtctac agcgtgatcc agtcgcagat   1080
caacgccgcg ctgtcggcca agcagggcat caggatcgac gctggcggta cgatctggt    1140 cgaccccacg ctatatggct atgccgtcgg cgatcccagg tggaaggaca gccccgagta   1200
tgcgctgctg agcaatctgg ataccttcag cggcaagctg tcgatcaagg attttctcag   1260
cggctcgccg aagcagagcg gggagctcaa gggcctcagc gatgagtacc ccttcgagaa   1320
ggacaacaac ccggtcggca atttcgccac cacggtgagc gaccgctcgc gtccgctgaa   1380
cgacaaggtc aacgagaaga ccaccctgct caacgacacc agctcccgct acaactcggc   1440 ggtcgaggc ctcaaccgct tcatccagaa atacgacagc gtcctgcgcg acattctcag   1500
cgcgatctag aggtatccat gaaccagcaa gcgaccccct tccgacaccga ccagcaacag   1560 gcgctggagg ccttcctgcg cgacggcggc accctggcga tgcttcgcgg actcagcgag   1620
gacaccctgg agcagctcta tgcgctgggc ttcaaccagt accaggcggg caagtgggac   1680
gacgcgcaga agatcttcca ggcactgtgc atgctcgacc actacgacgc ccgctacttt   1740
ctcggtctgg gcgcctgccg ccagtccctc ggtctctatg agcaggccct gcagagctac   1800
agctacggcg cgctgatgga catcaacgag ccgcgctttc ccttccatgc cgccgagtgc   1860
cacctgcaac tgggtgatct cgacggagcc gagagtggct tctactcggc ccgggccctg   1920
gccgcggcac agccggcgca cgaggccctg ccgcgcgtg ccggcgccat gttggaagcc   1980
gtaaccgcga gaaaggatcg aacatatgaa tccgataacg cttgaacgcg ccggactgcc   2040
ctacggggtg gccgacgccg gggatatccc ggcgctcggc aggccggtcg cgagggatgt   2100
cgagagtctg cgggtggagc gcctggcgg ccggccgcg gcttccgcga gcggcacggg    2160
ggtggcgctg acgccgccgt ccgcagccag ccagcagcgc ctggaggtcg ccaatcgtgc   2220
ggagatcgcc agcctggtgc aagcagtggg cgaggatgtc ggactggcgc ggcaggttgt   2280
gctggccggc gcttcgacgc tgttgtccgc cggcctgatg tcgccgcagg cgttcgagat   2340
cgagctggcg aaaatcaccg cgcaagtcga gaaccagcag aagaaactca agctgaccga   2400
aatcgagcag gcgcgaaagc agaacctgca gaaaatggag gacaaccagc agaagatcag   2460
ggaatcggaa gaagccgcga agaagcccca gaagtccggt ctggcagcca aaatctttgg   2520
ttggatcagt gcaatagctt cgatcatcgt cggcgcaatc atggtggcaa ccggcgtcgg   2580
cgcggccgcg ggtgcactga tgatcgcggg cggtgtcatg ggagtggtct cccagtcggt   2640
acagcaggca gccgcggacg gattgatcag caaggaagtg atggaaaagc tcggcccggc   2700
actgatgggt atcgagatcg ccgtcgcgct gctggcggcg gtggtcagct tcggcggctc   2760
agcggtcggc gggctggcca gactgggcgc gaagatcggc ggcaaggcgg ccgagatgac   2820
cgccagcctg gcgagcaagg tcgccgacct gggcggcaag ttcggcagtt tggccggcca   2880
atcgctgtcg cactcgctga aactcggcgt gcaggtttcc gacctgaccc tggacgtcgc   2940
```

-continued

```
caacggcgcg gcccaggcca ctcattcggg attccaggcg aaggccgcga accgccaggc    3000
cgacgtgcag gaatcgcgtg ccgacctgac caccctgcag ggcgtgatcg agcgcctgaa    3060
ggaagagctg agccgcatgt gcatgctgga agcattccag gaaatcatgg agcggatctt    3120
cgccatgctc caggccaagg gtgaaaccct gcacaacctg tccagccgac cggcagcgat    3180
ctgaggagac gtcacatgat cgacacgcaa tattccctgg cggctaccca ggccgcgatc    3240
ccctccgagc cgatcgctcc cggcgccgcc gggcgttccg tcggcacgcc gcaagcggct    3300
gcggacctgc cgcaggtgcc ggccgcgcgg gccgaccggg tcgaactgaa cgctccgcgc    3360
caggtgctcg acccggtgcg catggaagcg gccggcagcg agctggacag cagcgtcgag    3420
cttctgctga ttctcttccg catcgcgcag aaagcgcgcg agctgggcgt gctccagcgc    3480
gacaacgaga accagtcgat catccacgcg cagaaggcgc aggtggacga gatgcgcagc    3540
ggcgccacgc tgatgatcgc catggcggtg atcgctggcg tcggcgcatt ggcctcggcg    3600
gtggtcggca gcctcggcgc gttgaagaac ggcaaggcca tcagtcagga gaagaccctg    3660
cagaagaaca tcgatgggcg caacgaactg atcgacgcga agatgcaggc gcttggcaag    3720
acctccgacg aggatcgcaa gatcgtcggc aaggtctggg cggcggacca ggtgcaggac    3780
agtgtggcgt tgcgtgcggc gggccgtgcc ttcgagagcc gcaacggcgc cctgcaggtg    3840
gccaacacgg tgatccagtc cttcgtccag atggccaacg cctcggtcca ggtgcgccag    3900
ggcgaatcgc aggcgggcgc ccgggaagga gaggtcaacg ccaccatcgg gcagagccag    3960
aagcagaagg tcgaggacca gatgagcttc gatgccggct tcatgaagga cgtcctgcag    4020
ctcatccagc agtacaccca gagccataac caggcctggc gtgcggcggc cggagtggtc    4080
tgagccgtct ccgcgcggga ggaaaaggcc acagcgatgt ggcttttttc ttaaaagaaa    4140
agtctctcag tgacaaaagc gatgcata                                      4168
```